US012575866B2

(12) United States Patent
Maestro et al.

(10) Patent No.: US 12,575,866 B2
(45) Date of Patent: Mar. 17, 2026

(54) INTRAMEDULLARY IMPLANT FOR TRANSVERSE OSTEOTOMY

(71) Applicant: NOVASTEP, Rennes (FR)

(72) Inventors: Michel Maestro, Nice (FR); Martin Schramm, Nice (FR); Pietro Spennacchio, Luxembourg (LU); Marc Augoyard, Tassin la Demi Lune (FR); Romain Augoyard, Tassin la Demi Lune (FR); Thimothée Bissuel, Lyons (FR); Tristan Meusnier, Saint Etienne (FR); Prikesht Mukish, Saint Genis Laval (FR); Stéphanie Valentin, Lyons (FR); Thomas Sean Roukis, Onalaska, WI (US); Rémi Le Besque, Bruz (FR); Loïc Girod, Goven (FR); Grégory Gledel, Paris (FR)

(73) Assignee: NOVASTEP, Rennes (FR)

( * ) Notice: Subject to any disclaimer, the term of this patent is extended or adjusted under 35 U.S.C. 154(b) by 907 days.

(21) Appl. No.: 17/634,483

(22) PCT Filed: Aug. 7, 2020

(86) PCT No.: PCT/FR2020/051448
§ 371 (c)(1),
(2) Date: Feb. 10, 2022

(87) PCT Pub. No.: WO2021/028636
PCT Pub. Date: Feb. 18, 2021

(65) Prior Publication Data
US 2022/0296285 A1    Sep. 22, 2022

(30) Foreign Application Priority Data

Aug. 12, 2019    (FR) ...................................... 19/09154

(51) Int. Cl.
*A61B 17/72* (2006.01)
*A61B 17/17* (2006.01)
(Continued)

(52) U.S. Cl.
CPC ...... *A61B 17/7291* (2013.01); *A61B 17/1725* (2013.01); *A61B 17/1728* (2013.01);
(Continued)

(58) Field of Classification Search
CPC . A61B 17/7291; A61B 17/72; A61B 17/1725; A61B 17/8866; A61B 17/92; A61B 17/921; A61B 2017/565
See application file for complete search history.

(56) References Cited

U.S. PATENT DOCUMENTS 10,517,655 B2 * 12/2019 Lundquist .......... A61B 17/8061
2002/0143337 A1 * 10/2002 Orbay ................ A61B 17/7208
606/62
(Continued)

FOREIGN PATENT DOCUMENTS

EP      1 952 776 A1    8/2008
EP      3 476 319 A2    5/2019
(Continued)

OTHER PUBLICATIONS

May 9, 2023 Search Report Issued in Spanish Patent Application No. 202290009.
Feb. 10, 2021 International Search Report issued in International Application No. PCT/FR2020/051448.
Feb. 10, 2021 Written Opinion issued in International Application PCT/FR2020/051448.

*Primary Examiner* — Eduardo C Robert
*Assistant Examiner* — Holly Joanna Lane
(74) *Attorney, Agent, or Firm* — Eversheds Sutherland (US) LLP

(57)            ABSTRACT
An implant, of intramedullary implant type, suited for securing a first bone fragment to a second bone fragment following transverse osteotomy, includes: a plate having a
(Continued)

planar lateral face shaped to be secured to the second bone fragment, a shank shaped to be inserted into a medullary canal of the first bone fragment, and an intermediate portion, connecting the plate to the shank, the implant being characterized in that the shank is a solid of revolution centred on a longitudinal axis, the longitudinal axis being parallel to the lateral face of the plate.

31 Claims, 16 Drawing Sheets

(51) Int. Cl.
    *A61B 17/56*          (2006.01)
    *A61B 17/88*          (2006.01)
    *A61B 17/92*          (2006.01)
(52) U.S. Cl.
    CPC ...... *A61B 17/7233* (2013.01); *A61B 17/8866*
        (2013.01); *A61B 17/921* (2013.01); *A61B*
                        *2017/565* (2013.01)

(56) References Cited

U.S. PATENT DOCUMENTS

| | | | | |
|---|---|---|---|---|
| 2009/0317771 | A1* | 12/2009 | Anitua Aldecoa ... | A61C 8/0089 |
| | | | | 433/165 |
| 2016/0074079 | A1* | 3/2016 | Leemrijse ........... | A61B 17/809 |
| | | | | 606/291 |
| 2016/0354124 | A1 | 12/2016 | Bucci et al. | |
| 2016/0354127 | A1 | 12/2016 | Lundquist et al. | |
| 2017/0020537 | A1 | 1/2017 | Tuten | |
| 2018/0028242 | A1* | 2/2018 | Parekh .............. | A61B 17/8061 |
| 2018/0070995 | A1* | 3/2018 | Kay ................... | A61B 17/8061 |
| 2019/0125418 | A1* | 5/2019 | Muller ............... | A61B 17/164 |
| 2020/0015865 | A1* | 1/2020 | Lamm ................. | A61B 17/151 |
| 2020/0129304 | A1* | 4/2020 | Korman .............. | A61F 2/4225 |

FOREIGN PATENT DOCUMENTS

| | | | |
|---|---|---|---|
| FR | 3 004 920 | A1 | 10/2014 |
| WO | 2012/103335 | A1 | 8/2012 |

* cited by examiner

[Fig. 1]
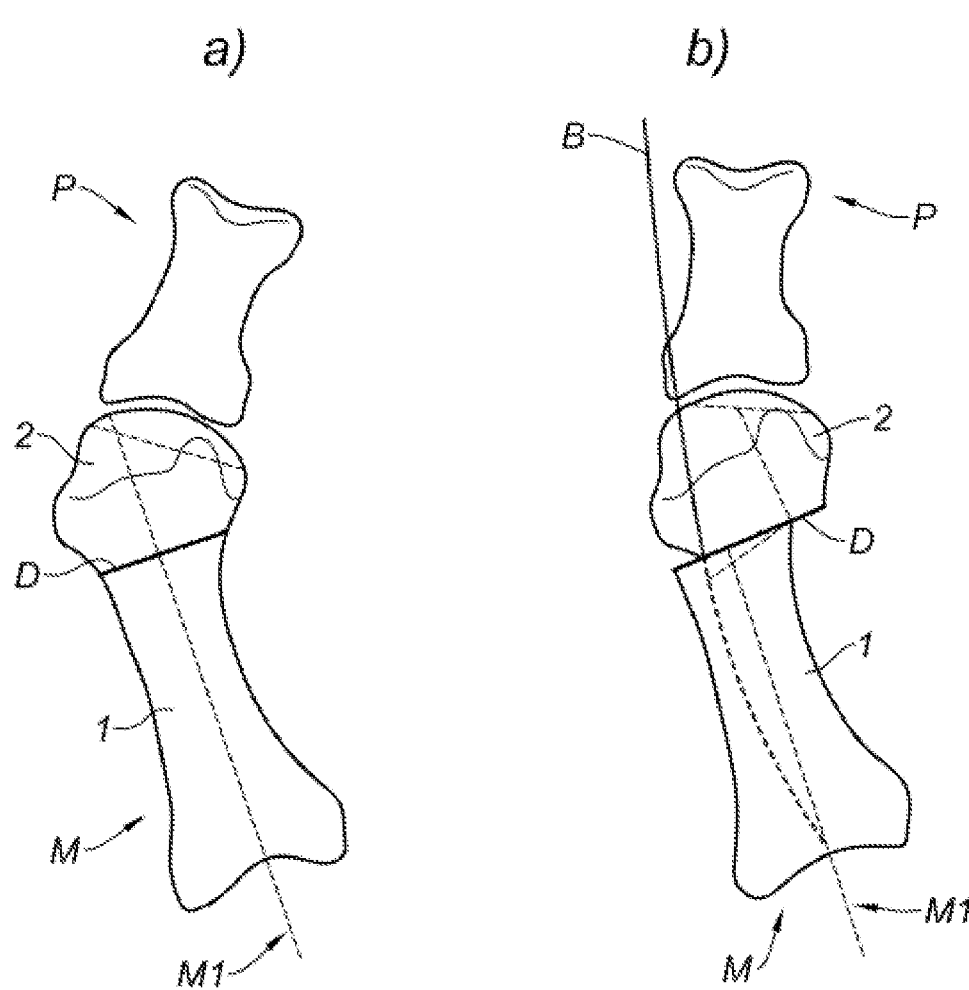
[Fig. 2]
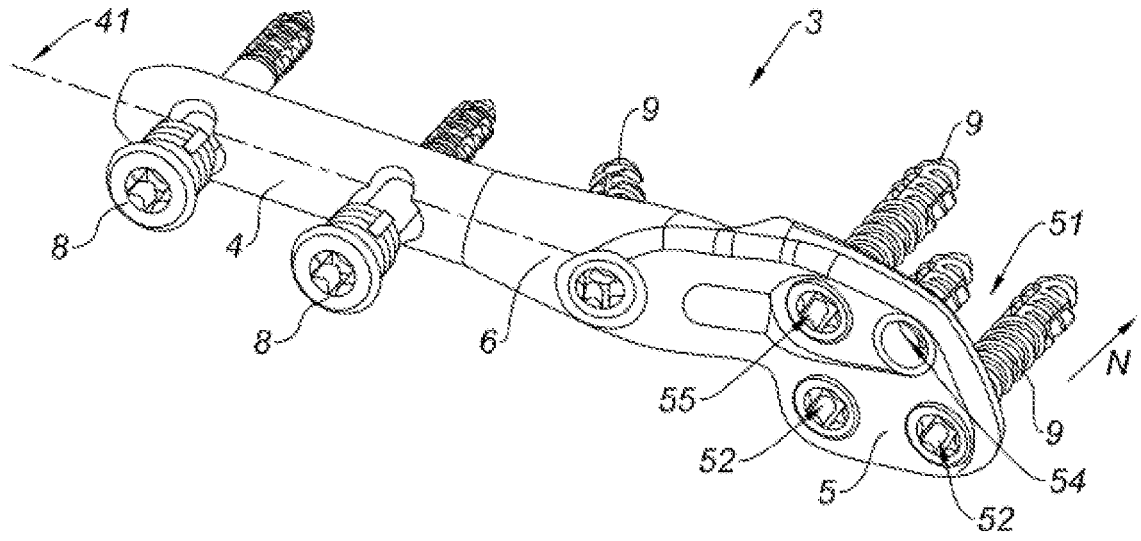

[Fig. 3]
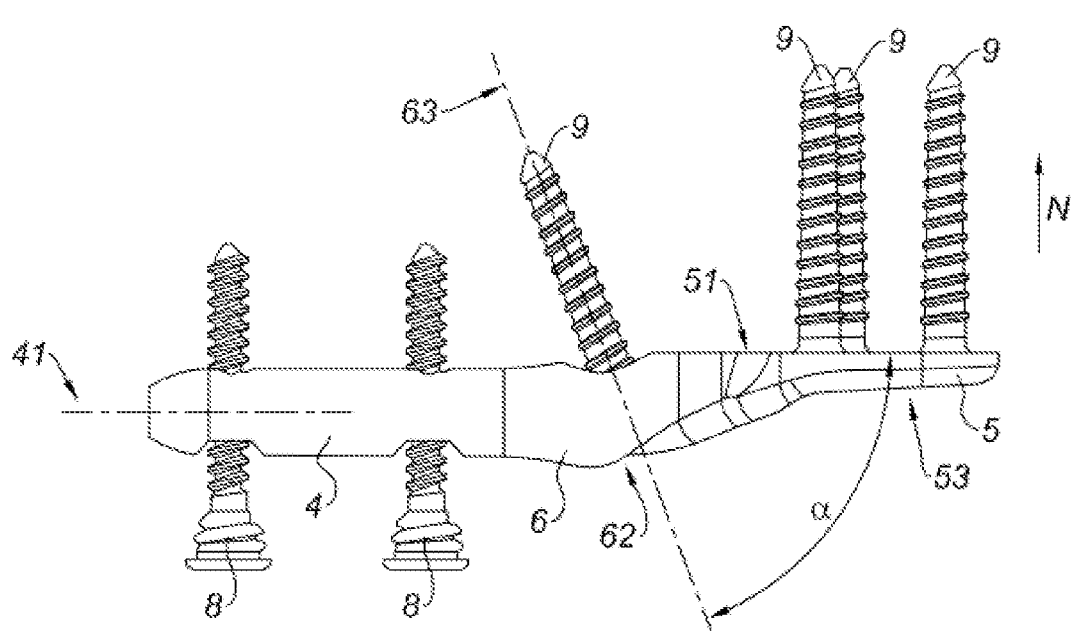
[Fig. 4]
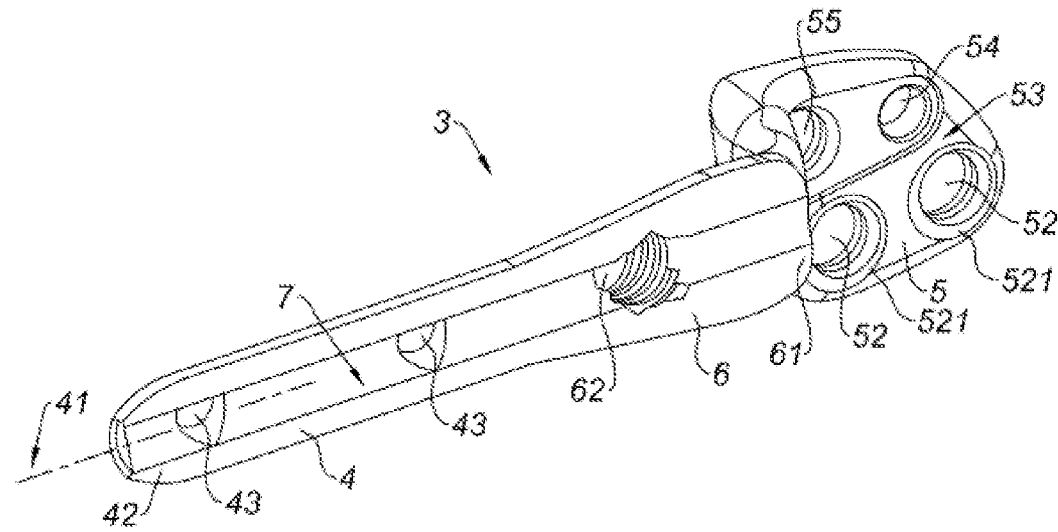

[Fig. 5]
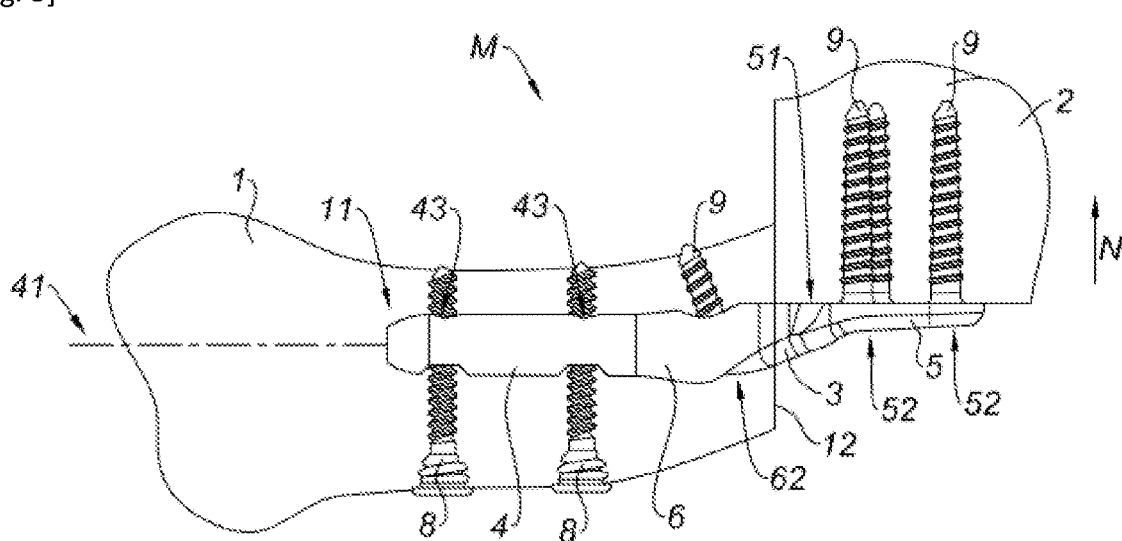
[Fig. 6]
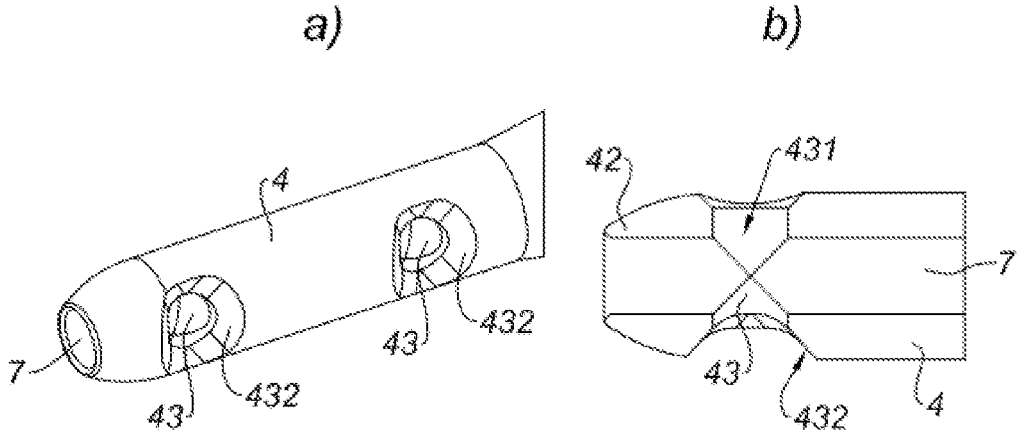
a)           b)

[Fig. 7]
a)
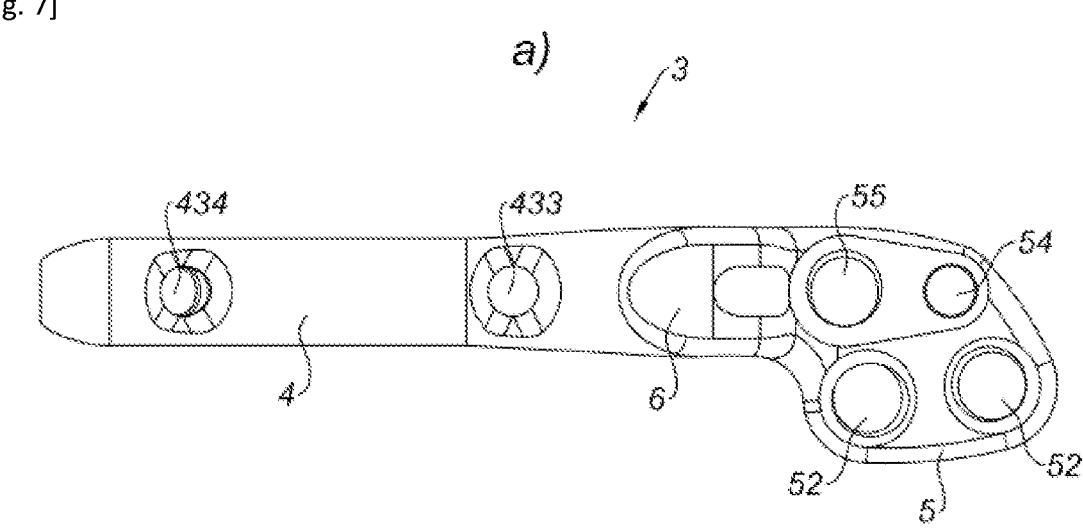
b)
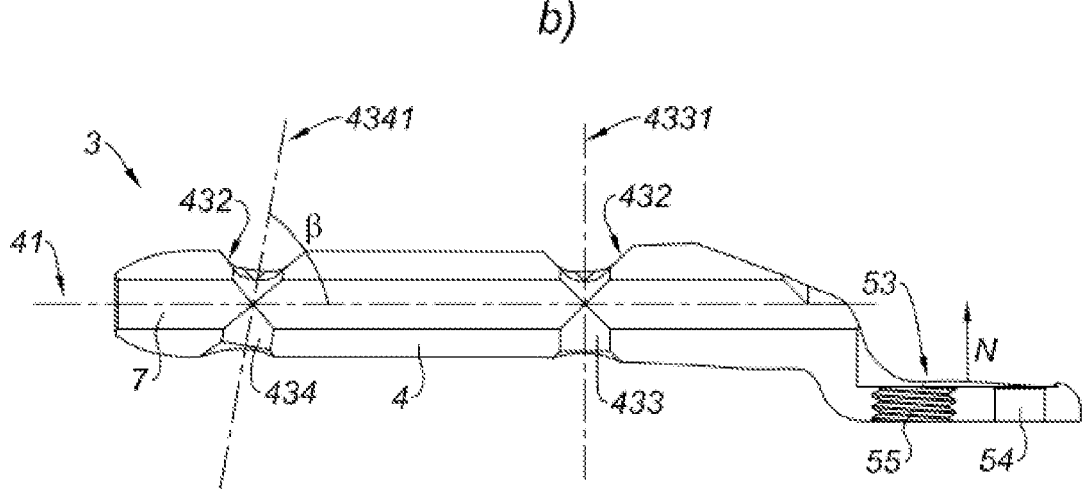

[Fig. 8]
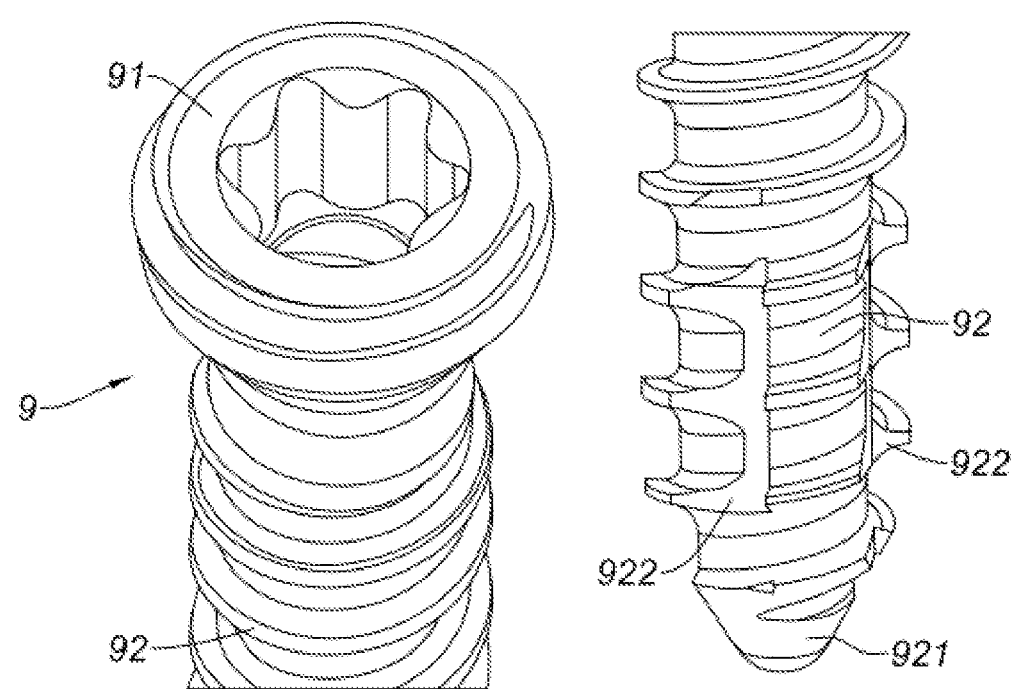
[Fig. 9]
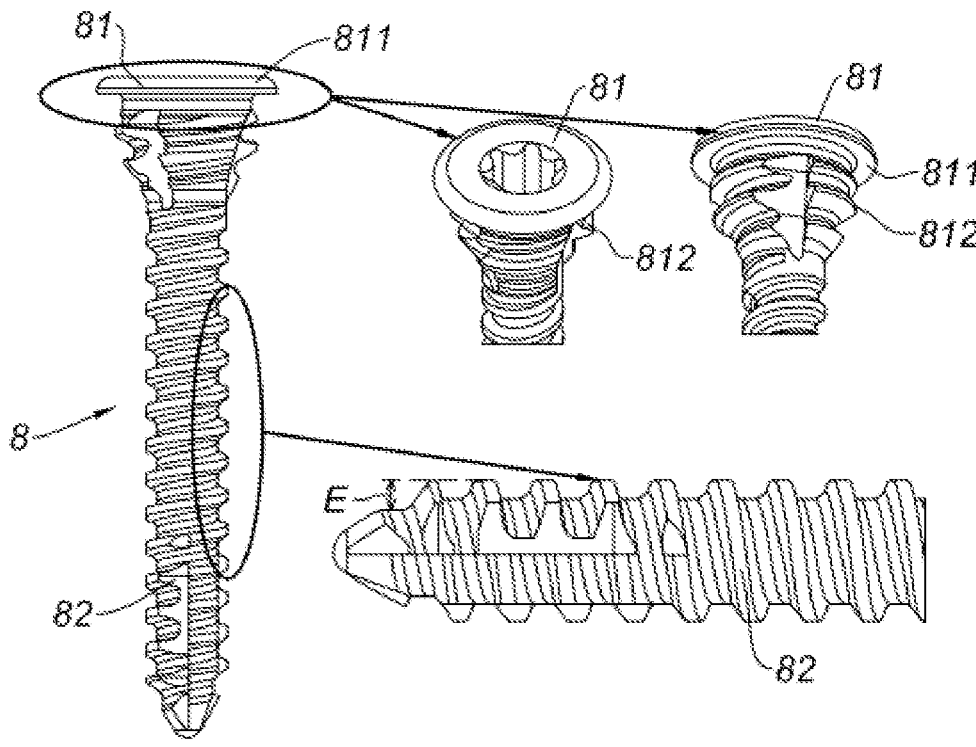

[Fig. 10]
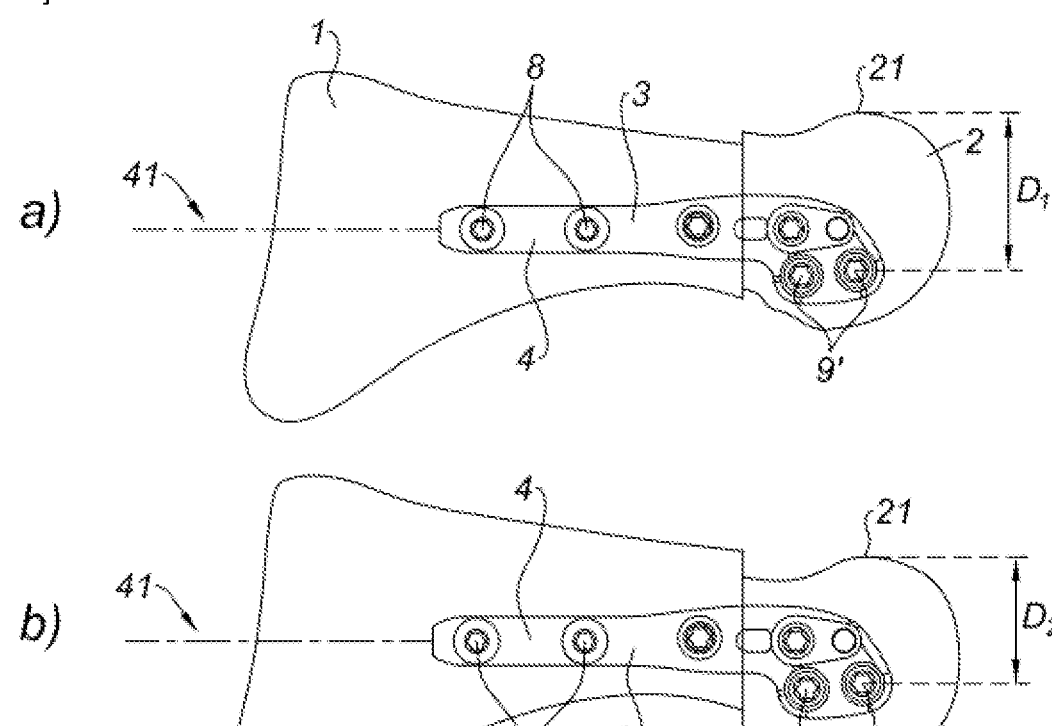
[Fig. 11]
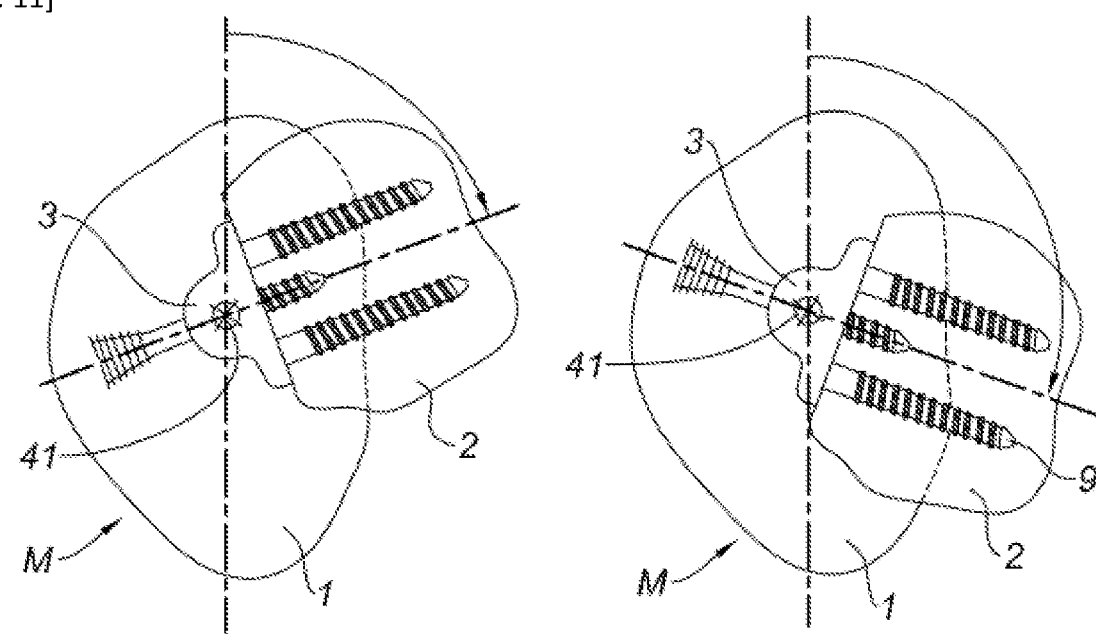

[Fig. 12]
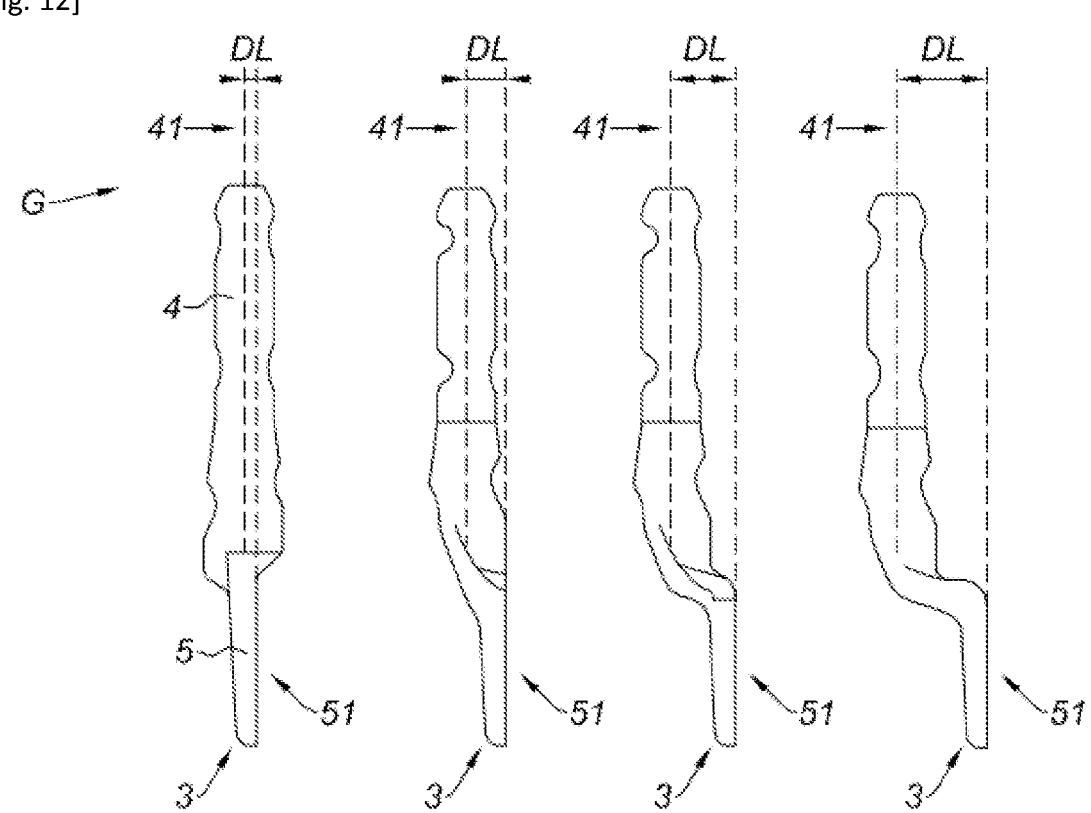
[Fig. 13]
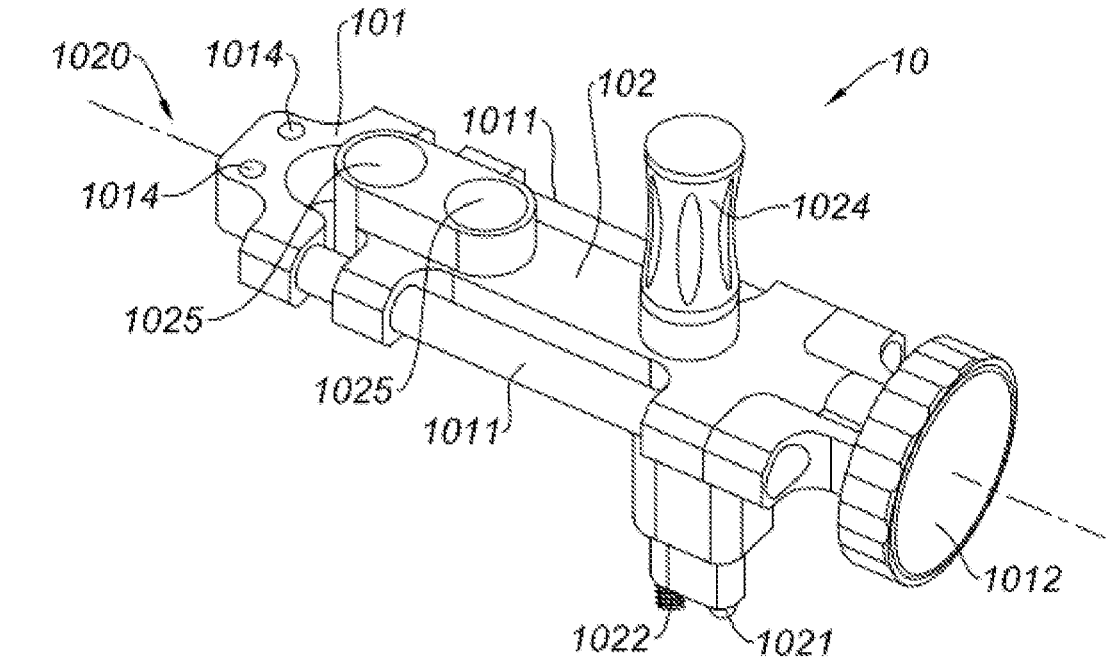

[Fig. 14]
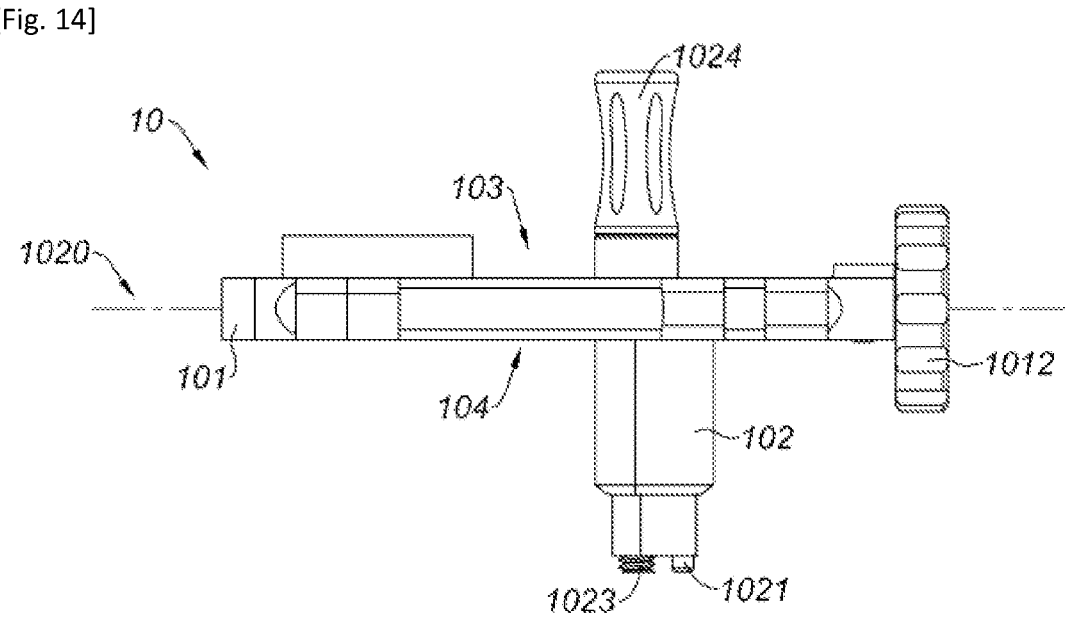
[Fig. 15]
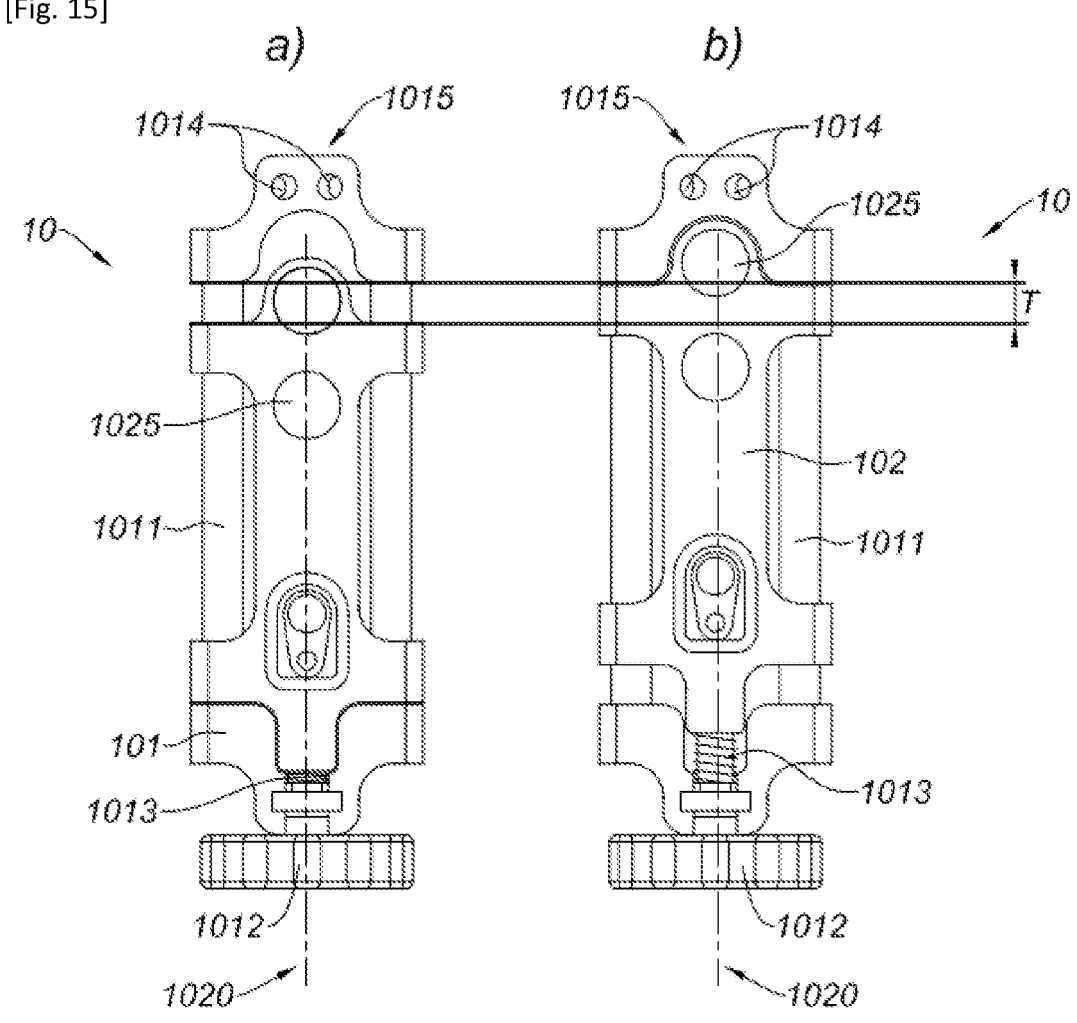

[Fig. 16]
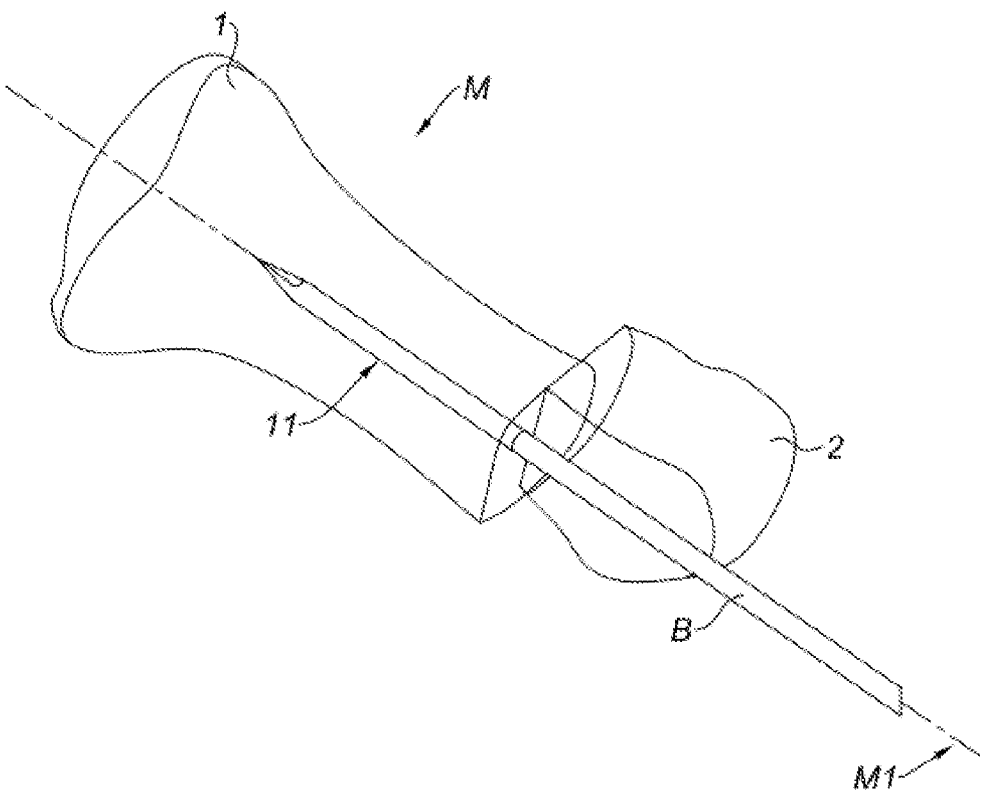
[Fig. 17]
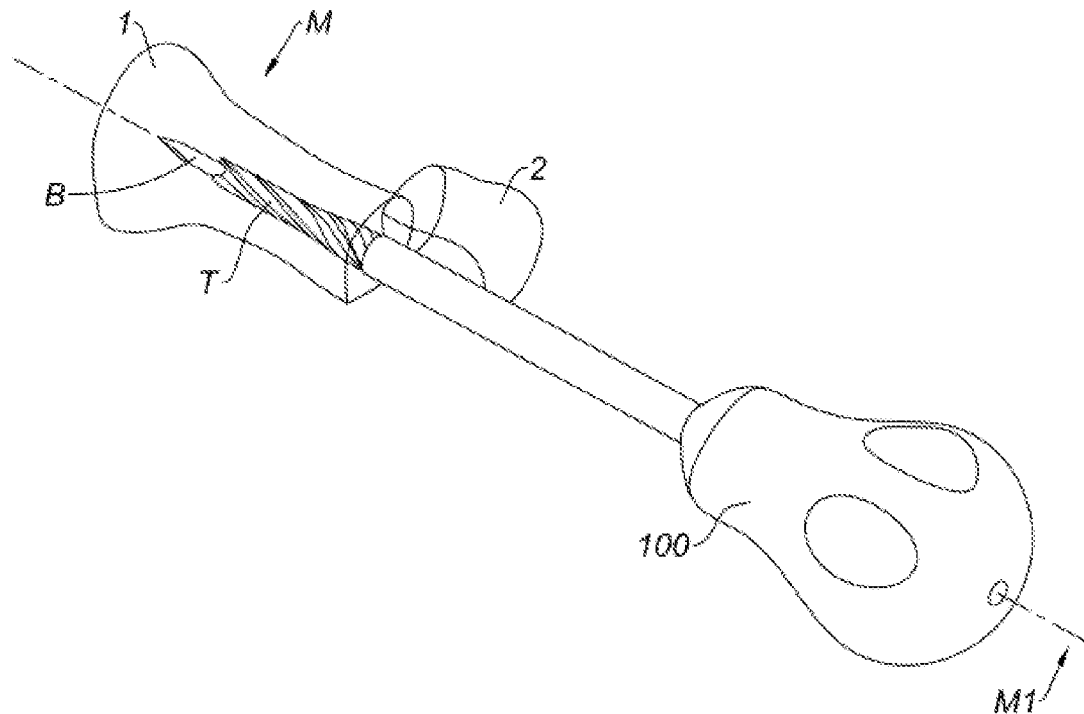

[Fig. 18]
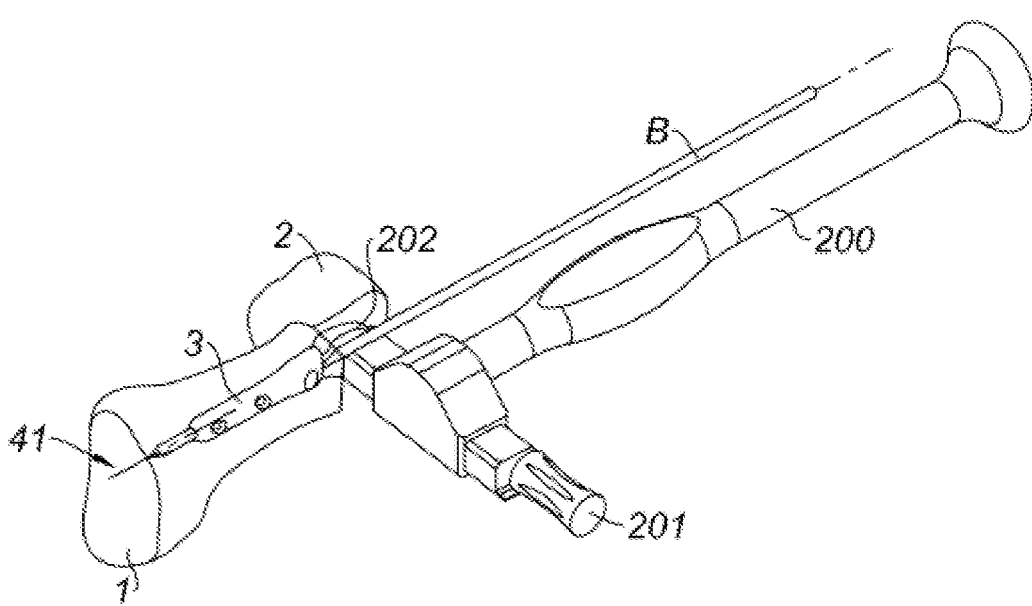
[Fig. 19]
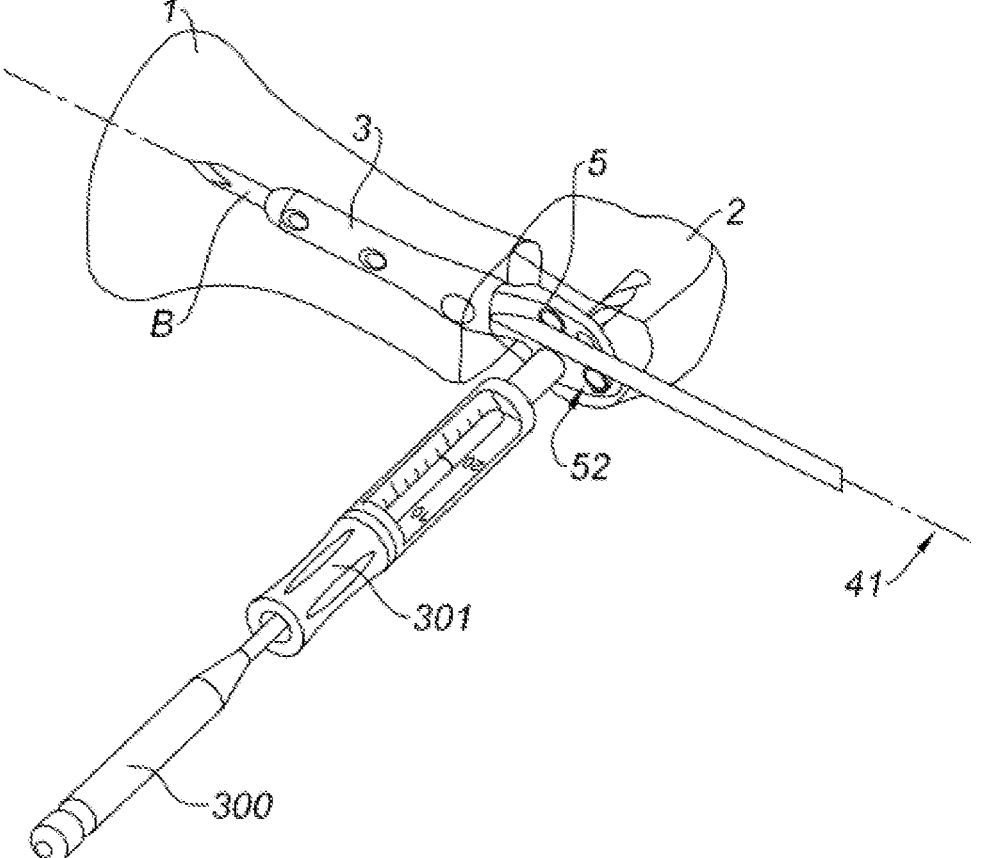

[Fig. 20]
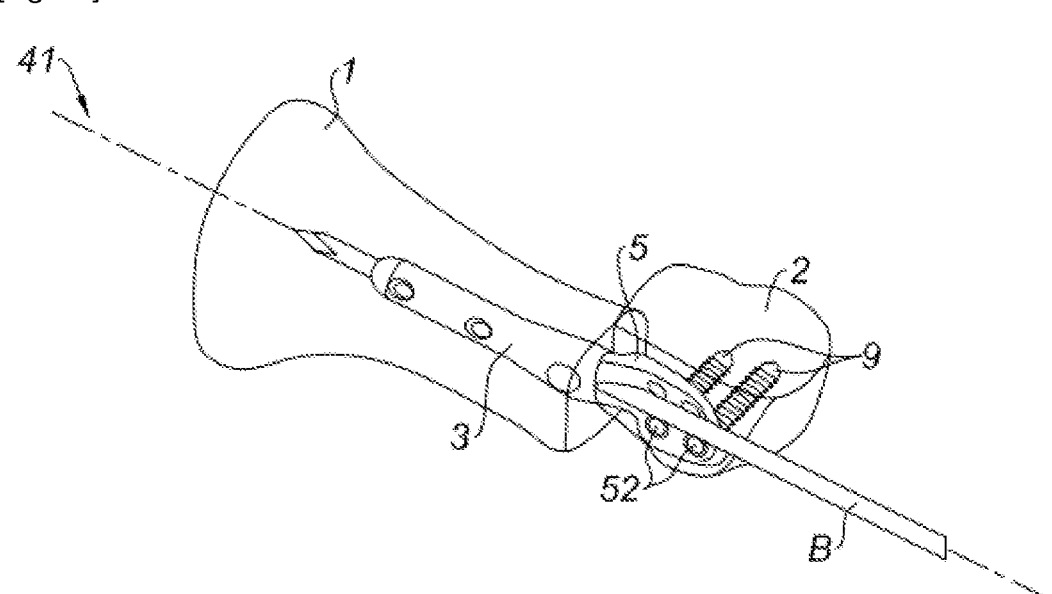
[Fig. 21]
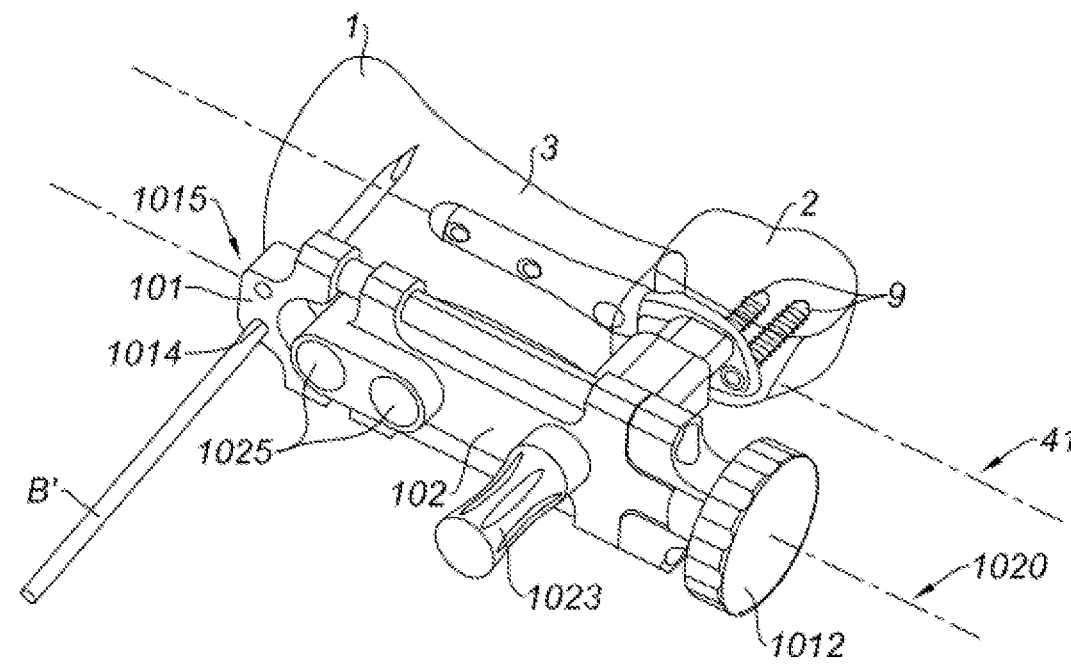

[Fig. 22]
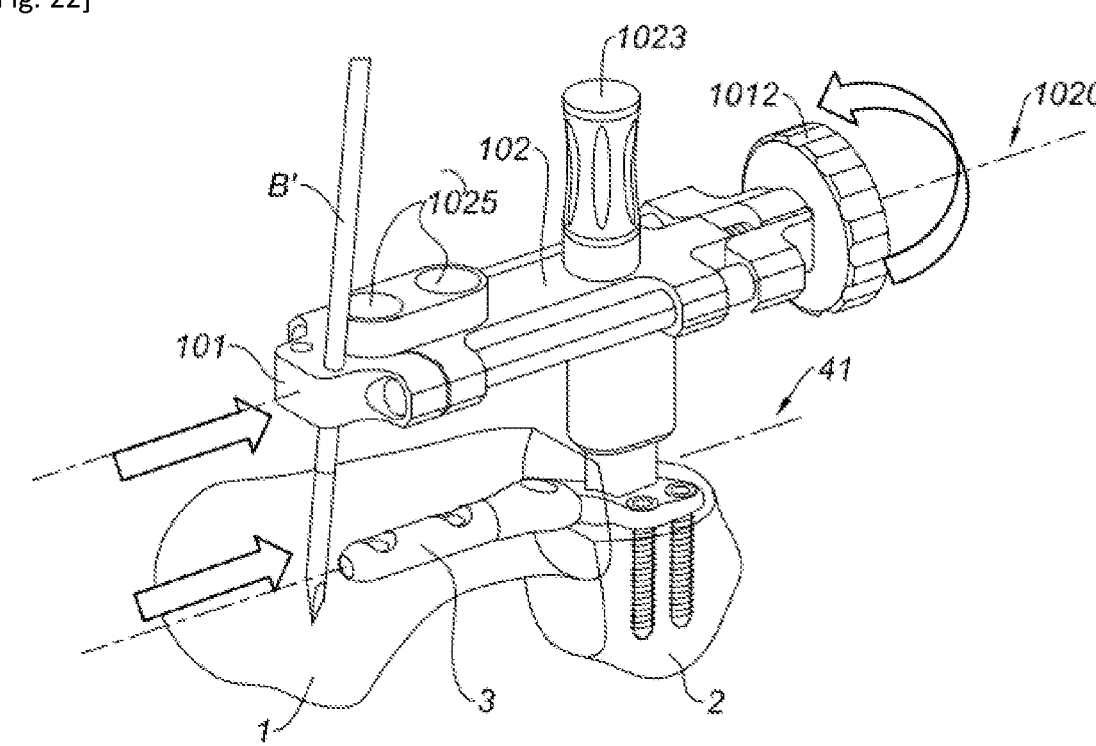
[Fig. 23]
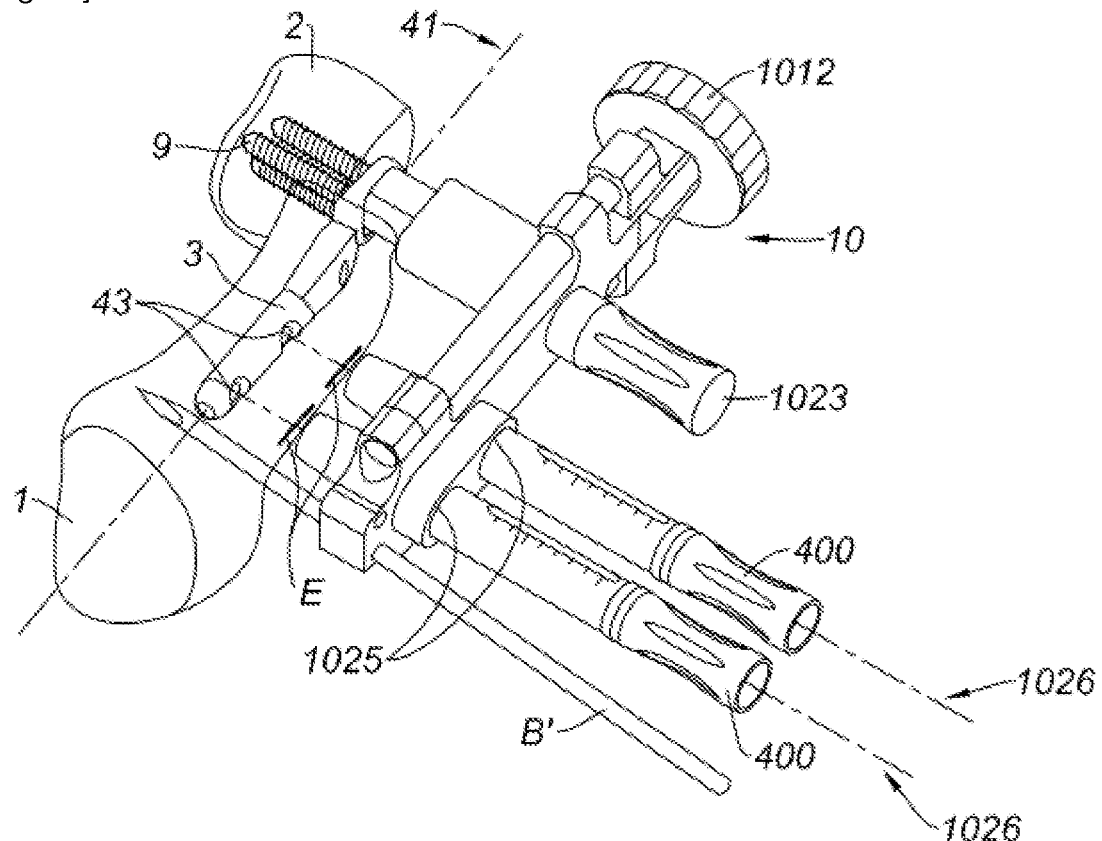

[Fig. 24]

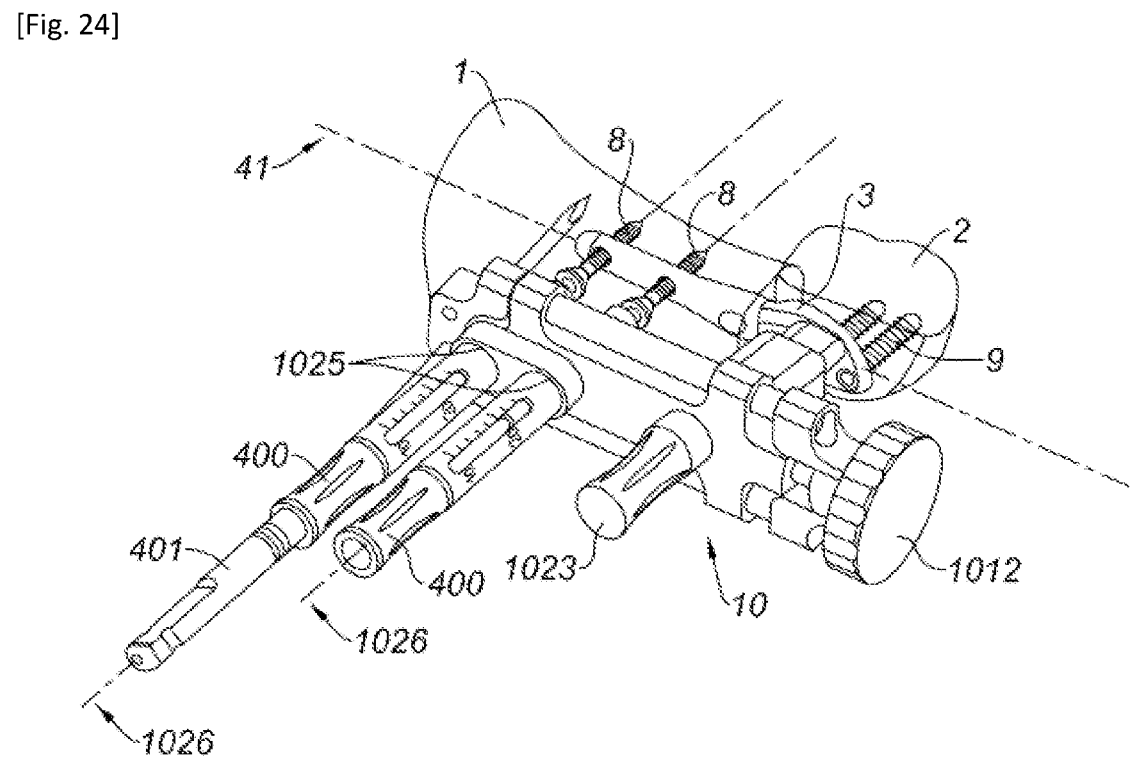

[Fig. 25]
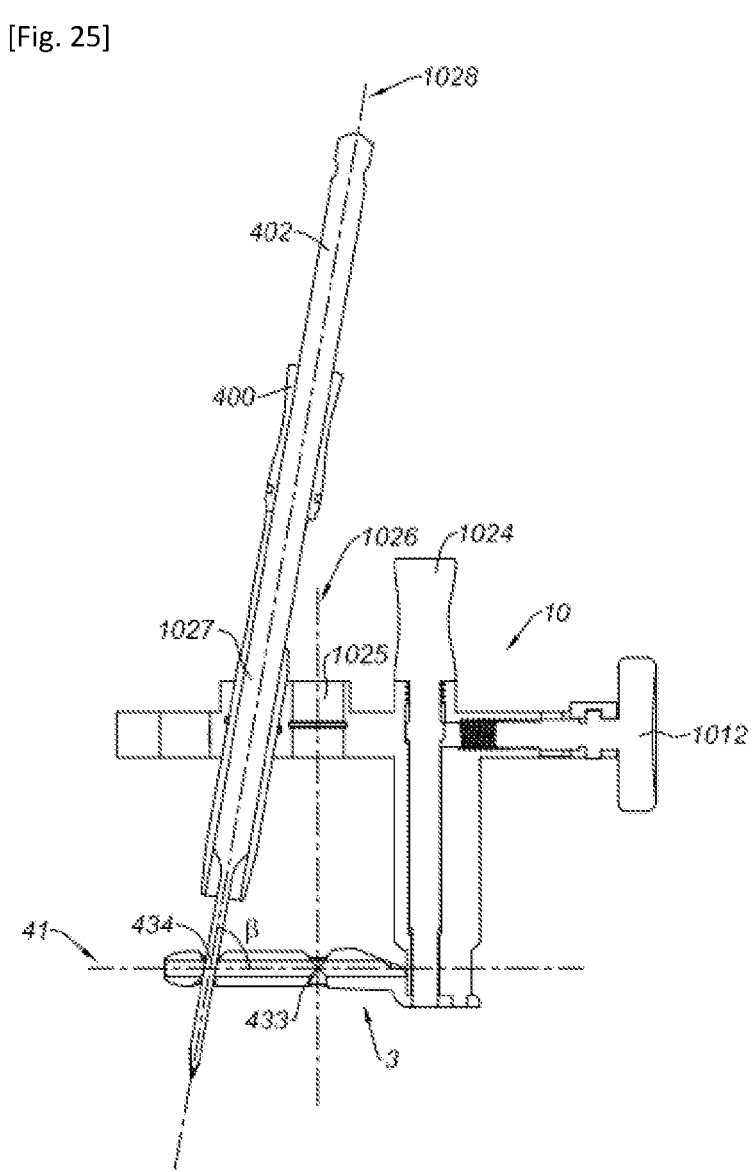

[Fig. 26]
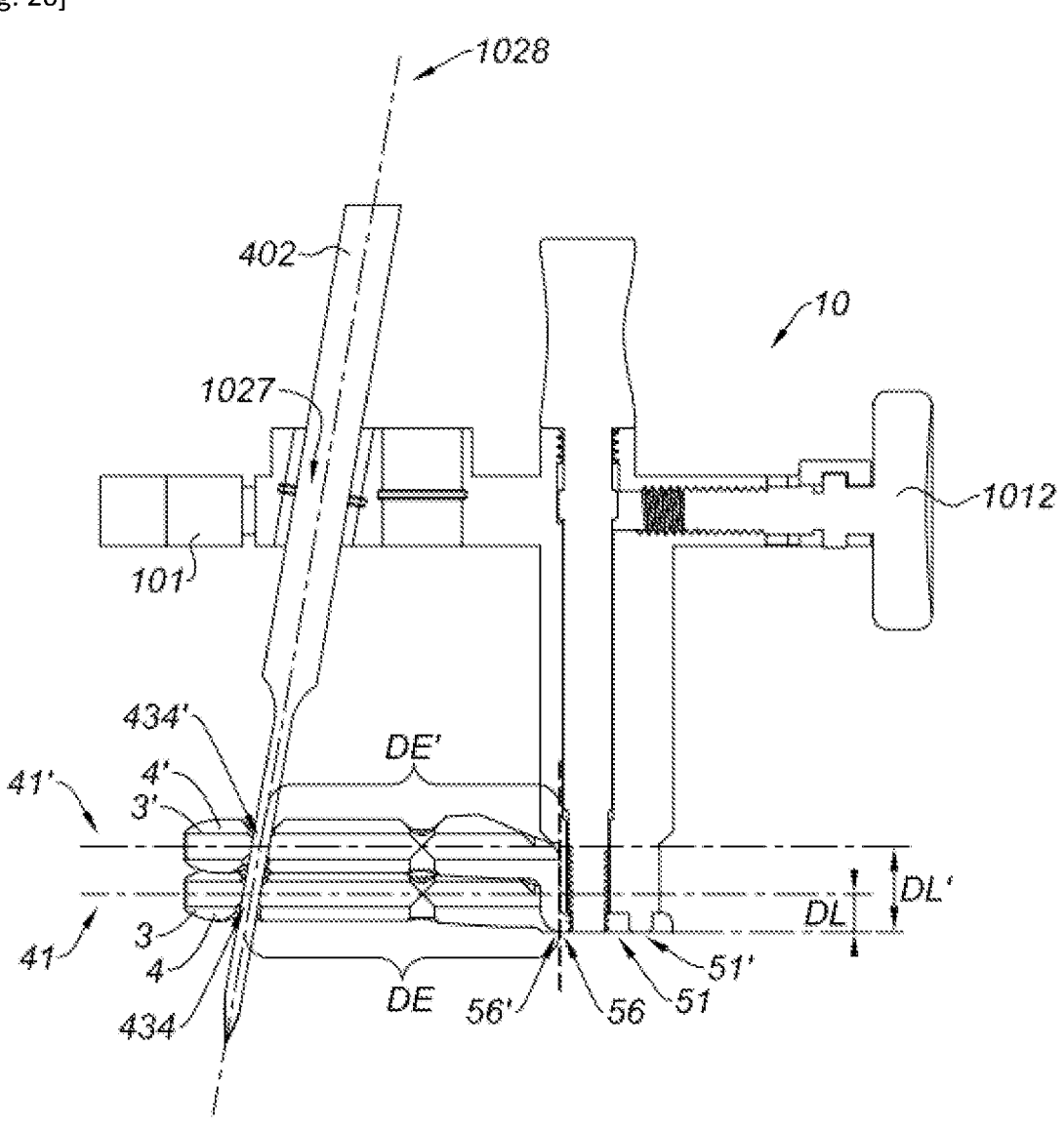

[Fig. 27]
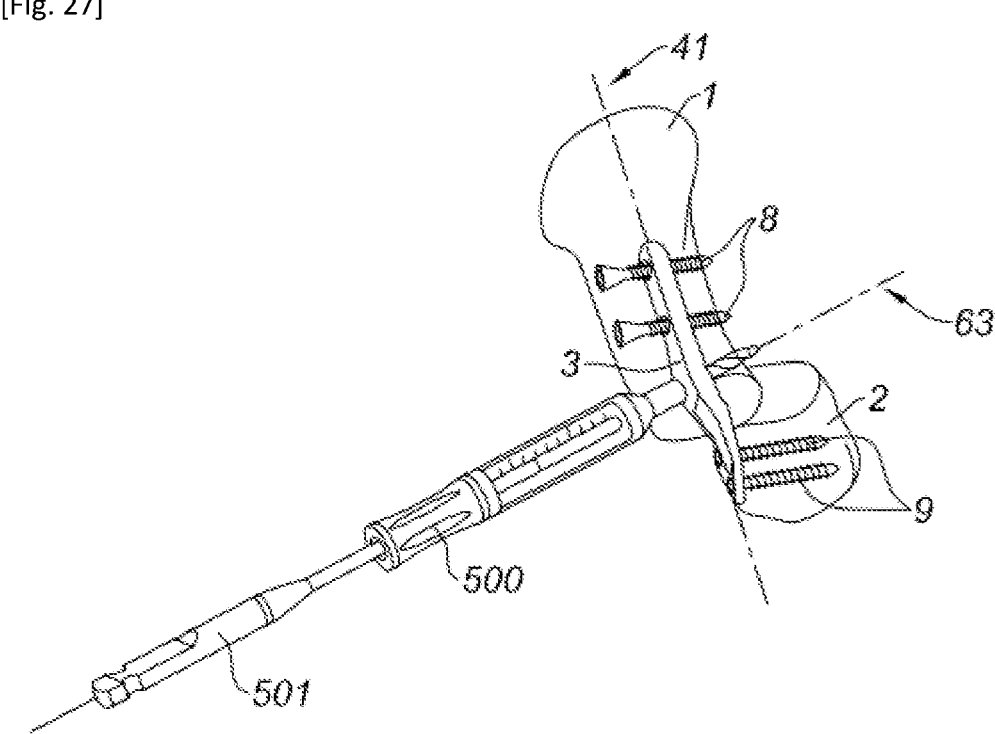
[Fig. 28]
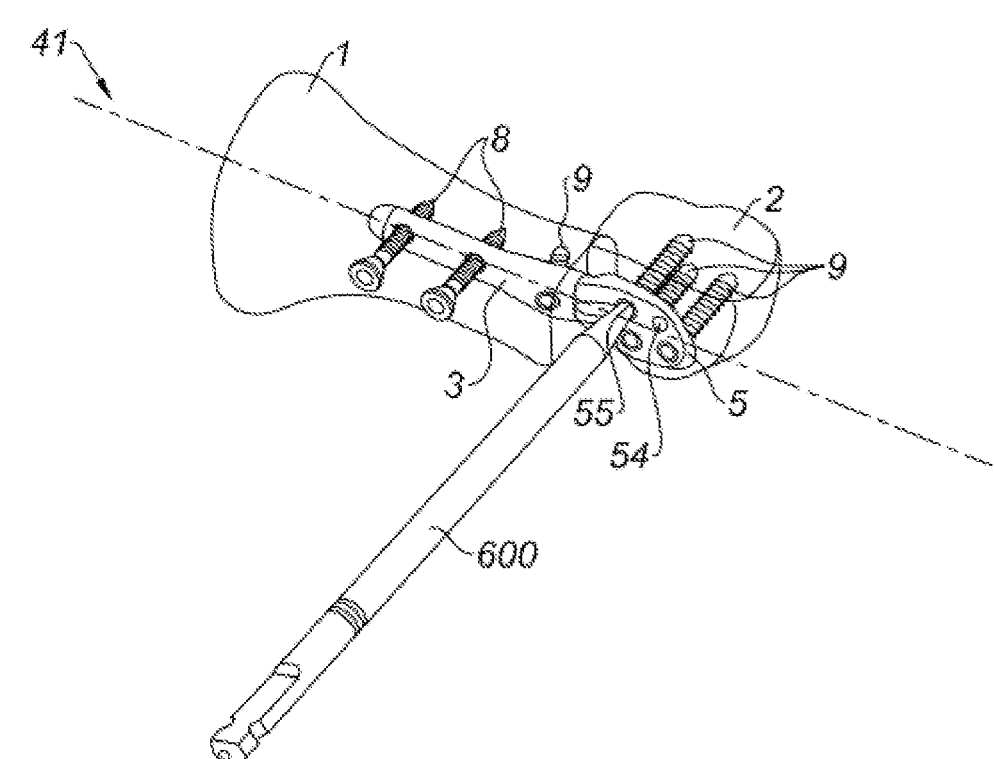

INTRAMEDULLARY IMPLANT FOR TRANSVERSE OSTEOTOMY

The present invention concerns a surgical implant suitable for the treatment of a hallux valgus by transverse osteotomy.

The deformation called hallux valgus is one of the most common deformations of the forefoot and refers to a deviation of the big toe (hallux) towards the other toes.

More exactly, the hallux valgus corresponds to a deviation «inward» of the first metatarsal (that is to say towards the other foot) and a deviation «outside» of the first phalanx of the big toe (that is to say, towards the other toes).

The appearance of this deformation, which mainly affects women, can be favored by many factors, in particular the frequent wearing of shoes with heels, a particular morphology of the feet, or even genetic heredity.

The consequence of this deformation is the creation of a bony protrusion from the end of the first metatarsal to the medial edge of the foot, commonly known as a «bunion».

The hallux valgus can therefore be a source of many inconveniences for the affected person: in addition to being unsightly, the hallux valgus can result in pain when walking at the level of the big toe or the arch of the foot (possibly with the appearance of calluses under the forefoot), as well as by difficulty in putting on because of the induced triangular shape of the forefoot, incompatible with many models of shoes.

In addition, the bony protrusion of the end of the first metatarsal causes friction of the skin in contact with the medial edge of the shoe: this prolonged friction can lead to inflammation of the skin and the appearance of bursitis filled with liquid, susceptible to be infected.

Although it is possible to relieve these pains by wearing orthopedic soles or adapted shoes, surgery is often necessary to treat the hallux valgus to free those affected from the daily handicap caused by this deformation.

There are several different surgical techniques suitable for the treatment of hallux valgus, but their common goal remains to correct the deformations and to more harmoniously distribute the mechanical stresses exerted on the forefoot.

In particular, percutaneous or «open» surgeries can be performed for the treatment of the hallux valgus.

Among the «open» surgical techniques, it is known practice to perform a transverse osteotomy (also called «Bosch osteotomy»), consisting in cutting the head of the metatarsal perpendicular to its longitudinal axis.

Thus, the severed head of the metatarsal is then displaced in lateral translation with respect to the diaphysis of the metatarsal so as to correct the deformation of the foot and realign the metatarsal and the first phalanx.

Once this translation has been carried out, the head of the metatarsal is usually maintained in its new position thanks to an implant generally having two parts:

a proximal part, inserted into the medullary canal of the diaphysis of the metatarsal and a distal part, fixed on the head of the metatarsal.

For example, document FR3004920 describes such an intramedullary implant including a fixing plate adapted to be screwed onto the head of the metatarsal and an elongated tail intended to be inserted into the medullary canal of the diaphysis of the metatarsal.

However, the implants known from the state of the art have the drawback of making it impossible to adjust in axial rotation (along the longitudinal axis of the metatarsal) the metatarsal head after the implant has been inserted into the medullary canal of the metatarsal diaphysis.

Indeed, the shape of the proximal part of these implants, inserted into the medullary canal of the diaphysis of the metatarsal, does not allow them to perform such a rotation without damaging said medullary canal.

In addition, since the proximal part of the implants is generally included in the same plane as the distal part, it is impossible to vary the position of the metatarsal head relative to the diaphysis of the metatarsal in the medial/lateral plane once these implants are inserted into the medullary canal of the metatarsal diaphysis.

Thus, in order to be able to position the head of the metatarsal with precision in relation to the diaphysis of the metatarsal, the implants already known require a very complex and require great precision surgical technique before inserting them into the medullary canal of the metatarsal diaphysis.

Finally, this surgical technique is usually unguided and very invasive, a wide approach being in fact mandatory to allow manipulation of the metatarsal and the implant.

Moreover, documents EP3476319, US2016/354124 and US2018/070995 are also known, which describe an implant, of the intramedullary implant type, including an extramedullary portion called platinum having a flat lateral face shaped to be fixed on a bone fragment, an intramedullary portion shaped to be inserted into a medullary canal of a first bone fragment, said intramedullary portion being a solid substantially of revolution centered on a longitudinal axis, and said longitudinal axis being parallel to the lateral face of the extramedullary portion which extends to the distal end of the intramedullary portion, and an intermediate portion connecting said plate to said intramedullary portion.

Although this type of implant makes it possible to adjust the position of the head of the metatarsal in axial rotation relative to the diaphysis of the metatarsal by causing the intramedullary portion to perform a rotational movement about its longitudinal axis, it is not guided and involves an invasive surgical technique.

The object of the present invention is to resolve all or part of these drawbacks, by proposing an implant which makes it possible to adjust in axial rotation the position of the head of the metatarsal relative to the diaphysis of the metatarsal once the implant is inserted into the medullary canal of the metatarsal diaphysis.

Another object of the invention is to provide an implant making it possible to vary the position of the head of the metatarsal in the medial/lateral plane.

Yet another object of the invention is to provide a dedicated surgical instrumentation, making it possible to guide the manipulation and the insertion of the implant in order to make these operations more precise, easier to perform and less invasive.

To this end, it proposes an implant, of the intramedullary implant type, suitable for fixing a first bone fragment on a second bone fragment, said implant including:

a plate having a flat lateral face shaped to be fixed on the second bone fragment, a keel shaped to be inserted into a medullary canal of the first bone fragment, the keel being a solid of revolution centered on a longitudinal axis, and said longitudinal axis being parallel to the lateral face of the plate, and an intermediate portion, connecting said plate to said keel, said implant being remarkable in that the plate includes a securing device making it possible to releasably secure said implant to a tool suitable for preparing the attachment of said implant on the metatarsal.

When such an implant is used for the treatment of a hallux valgus and following a transverse osteotomy (preferred scope of use of the invention), the first bone fragment corresponds to a diaphysis of a metatarsal and the second bone fragment corresponds to a head of this same metatarsal: the implant is then particularly suitable for fixing and maintaining in position this head of a metatarsal relative to this diaphysis of this same metatarsal following a transverse osteotomy: in position, the keel, located in the proximal part of the implant, is inserted into the medullary canal of the metatarsal diaphysis and the plate, located in a part distal to the implant, is attached on the head of the metatarsal.

Thanks to the specific structure of the keel, having the shape of a solid of revolution centered on a longitudinal axis, it is possible to make the implant perform a rotational movement about this same longitudinal axis once this implant is inserted into the medullary canal of the diaphysis of the metatarsal.

Indeed, the shape of the keel is invariant in rotation about this longitudinal axis:

the rotation of the keel in the medullary canal of the diaphysis of the metatarsal can thus be carried out without any additional deformation of this medullary canal, once the implant is inserted.

In this way, it is possible to adjust the position of the head of the metatarsal in axial rotation with respect to the diaphysis of the metatarsal by causing the keel to perform a rotational movement about its longitudinal axis after having inserted the latter in the medullary canal of the diaphysis of the metatarsal and fixed the plate on the head of the metatarsal.

Moreover, such a tool can, for example, make it possible to manipulate the implant from a distance or to guide the practitioner during steps of drilling and then of screwing the implant onto the metatarsal.

This tool, specially dedicated to the implant according to the invention, thus makes it possible to insert and fix said implant by a minimally invasive surgical technique, and to guide the practitioner during the operation.

The implant securing device is thus designed to cooperate with a complementary device for securing the tool, in order to allow a coupling of the implant to the tool.

According to one possibility, the keel has a cylindrical shape.

In one embodiment, the plate includes at least two threaded holes passing through the plate between the lateral face and an opposite medial face, each of said threaded holes having a housing opening onto the medial face and adapted to receive the head of an anchoring screw.

The plate can thus be fixed by screwing, using suitable anchoring screws and from the medial face of the implant, on the head of the metatarsal.

When the anchoring screws are completely screwed into the head of the metatarsal their respective heads are received in the corresponding housings of each threaded hole.

In this way, the anchoring screws do not protrude from the medial face of the implant and the implant retains a reduced thickness: the presence of these housings makes it possible to make the implant less invasive.

According to one possibility, the threaded holes extend in a direction normal to the lateral face.

According to one possibility, the plate includes an indexing means making it possible to index the position of the implant with respect to the tool with a view to secure the tool on the implant.

According to another possibility, the indexing means consists of an indexing orifice formed in the plate and opening out on the medial face.

According to yet another possibility, the securing device includes a threaded hole formed in the plate and opening onto the medial face.

According to yet another possibility, the threaded hole of the securing device:

crosses the plate between the medial face and the lateral face, has a housing opening onto the medial face adapted to receive the head of an anchoring screw.

The securing device thus makes it possible to position and orient the implant relative to the tool thanks to the indexing means, then to removably fix the tool on the implant (once the implant is positioned) thanks to, for example, a screw of the tool cooperating with the threaded hole of the securing device.

According to one characteristic, the threaded hole of the securing device extends in a direction normal to the lateral face of the plate.

Advantageously, the threaded hole of the securing device is identical to the threaded holes of the plate: it is thus possible, once the implant is fixed to the metatarsal and detached from the tool, to use this threaded hole of the securing device to strengthen the attachment of the plate on the metatarsal head by means of an additional anchoring screw.

In one embodiment, the keel has at least one hole passing through said keel in a cross direction, for example orthogonal, to the longitudinal axis and adapted to receive an anchoring screw.

According to one variant, the hole(s) of the keel have an internal thread, adapted to cooperate with an anchoring screw.

This or these holes make it possible, by screwing an anchoring screw into each of them, to fix the keel to the diaphysis of the metatarsal.

In particular, these anchoring screws, screwed from the medial cortex of the metatarsal diaphysis so as to pass through the implant keel in the medullary canal of the metatarsal diaphysis through the hole(s) of the keel, block any movement of rotation of the implant about the longitudinal axis of the keel.

Thus, this or these holes and these adapted anchoring screws make it possible to fix the position of the head of the metatarsal in rotation with respect to the diaphysis of the metatarsal once the position desired by the practitioner has been obtained by rotating the keel about its longitudinal axis.

According to one possibility, the hole(s) of the keel extend in a direction normal to the lateral face of the plate.

According to another possibility, the hole(s) of the keel extend in a direction not parallel to the direction normal to the lateral face of the plate.

According to another possibility, the hole(s) of the keel have a medial mouth provided with a peripheral chamfer.

The function of this peripheral chamfer is to facilitate the insertion of drills into the threaded holes of the keel, in order to make holes which then allow the anchoring screws to be inserted therein.

These guiding elements thus make it possible to facilitate the attachment of the implant on the metatarsal and to maintain a minimally invasive surgical technique.

Advantageously, the keel includes an inner conduit centered on the longitudinal axis, said inner conduit opening out at a proximal end of the keel, passes through the intermediate portion and opens out at a distal end of said intermediate portion.

The function of this inner conduit is to guide the insertion of the implant into the medullary canal of the diaphysis of the metatarsal.

Indeed, it is possible to insert a Kirschner wire beforehand into the medullary canal of the diaphysis of the metatarsal, then to «thread» on this wire, the keel of the implant: the wire therefore enters the inner conduit of the keel through the proximal end of the latter, and emerges from this same inner conduit at a distal end of the intermediate portion.

In this way, it is then easy to slide the implant along the wire to insert the keel of the implant into the medullary canal of the diaphysis of the metatarsal possibly by using a surgical impactor.

In one embodiment, the intermediate portion has a conical shape centered on the longitudinal axis.

The conical shape of the intermediate portion makes it possible to achieve the junction between the plate and the implant keel while having a large cross section: thanks to this, the intermediate portion offers high mechanical resistance in flexion and makes it possible to avoid deformation of the implant under physiological load conditions.

According to one possibility, the intermediate portion includes a hole which is formed passing through said intermediate portion, said hole extending in a direction not parallel to the direction normal to the lateral face of the plate.

This hole may optionally have an internal thread, so as to cooperate with an anchoring screw.

This hole thus fulfills two functions:

it allows the implant to be attached to the metatarsal diaphysis by screwing an anchoring screw into the lateral cortex of the metatarsal diaphysis and due to the non-orthogonality of the hole with the lateral face of the plate (fixed on the head of the metatarsal), the screwing of the anchoring screw in the hole makes it possible to exert an interfragmentary pressure by compressing the head of the metatarsal on the diaphyseal shaft of the metatarsal.

Advantageously, the threaded hole of the intermediate portion has a housing opening onto a medial face of the intermediate portion, said housing being adapted to receive the head of an anchoring screw.

As previously, once the anchoring screw has been fully screwed, from the medial face of the implant, into the threaded hole, the head of this anchoring screw is received in a suitable housing so that it does not protrude from the medial face of the intermediate portion.

This characteristic thus makes it possible to make the implant as less invasive as possible.

According to one possibility, the threaded hole of the intermediate portion extends in a direction forming an angle with the lateral face of the plate, whose measurement is comprised between 60° and 80°.

In one embodiment, the keel has at least two holes passing through said keel and adapted to receive an anchoring screw, the first of these holes extending in a direction parallel to the direction normal to the lateral face of the plate, and the second one of these holes extending in a direction not parallel to said normal direction.

In this embodiment, the second hole of the keel extends in a direction not orthogonal to the longitudinal axis, and obliquely with respect to the first hole of the keel: this second hole thus fulfills the same function as the threaded hole of the intermediate portion previously described.

In particular, this second hole makes it possible, in a similar manner, to fix (thanks to an anchoring screw) the implant on the diaphysis of the metatarsal while exerting an interfragmentary pressure by compressing the head of the metatarsal on the diaphyseal shaft of the metatarsal.

It is conceivable that this second hole is formed in the keel in combination with the threaded hole of the intermediate portion, or as a replacement of the latter.

The invention also concerns a range of implants comprising several implants as described above, said implants each having a lateral offset distance, separating the lateral face of the plate from the longitudinal axis, of distinct measurement.

This range of implants allows adjusting the position of the metatarsal head in relative to the metatarsal diaphysis in the medial/lateral plane.

Indeed, the greater the lateral offset distance (also called «step») of the implant according to the invention, the more the head of the metatarsal fixed to the plate of the implant, will be far from the longitudinal axis of the implant keel, and thus from the medullary canal of the metatarsal diaphysis.

Such a range of implants therefore allows a more precise correction of the hallux valgus and adapted to each patient, the practitioner being able to select before the surgical operation the implant of the range best suited to each particular deformation to be corrected.

According to one possibility, the implants have a lateral offset distance, whose measurement is comprised between 0 millimeters and 10 millimeters.

According to a variant, the implants are as described above and each have an offset distance, separating a proximal end of the plate from the second hole of the keel, of distinct measurement.

This characteristic makes it possible to secure each of the implants in the implant range with the same tool, this tool making it possible to manipulate each of them and being adapted to cooperate with their respective securing device.

Indeed, when the keel of each implant in the range has a second hole extending in a direction not orthogonal to the longitudinal axis, it is necessary to modify the position of this second hole along the keel according to the lateral offset distance, so that the same tool can effectively guide the practitioner during the drilling and then screwing steps of implants from the range of implants on the metatarsal, as will be described more precisely below.

The invention also concerns surgical instrumentation including a tool suitable for preparing the attachment, on a bone, of an implant as described above, said tool including:

a frame, having a distal part and a proximal part, a movable body, having a lower face and an opposite upper face, including a complementary securing device adapted to cooperate with the device for securing the plate, so as to fix the tool on the implant, and said movable body being movable in translation relative to the frame along a translation axis parallel to the longitudinal axis of the implant when the tool is attached to the implant, and a fastening device making it possible to fix said frame on the first bone fragment to which the implant is also fixed.

In the particular context of the treatment of a hallux valgus, the fastening device makes it possible to fix the frame on the diaphysis of a metatarsal to which the implant is also fixed, as previously described.

As previously mentioned, the tool allows (once it has been secured to the implant thanks to the cooperation between the securing device of the implant and the complementary device for securing the tool) to manipulate the implant remotely or to guide the practitioner during the steps of drilling and then screwing the implant on the metatarsal.

In addition, thanks to the presence of the movable body, the tool makes it possible to apply interfragmentary compression between the head of the metatarsal and the diaphyseal shaft of the metatarsal.

Indeed, the frame is fixed to the diaphysis of the metatarsal via the fastening device while the movable body is secured to the head of the metatarsal (because the movable body cooperates with the securing device of the implant located on the plate thereof, itself being fixed to the head of the metatarsal): the translational movement of the movable body relative to the frame therefore amounts to displace in translation the head of the metatarsal relative to the diaphysis of the metatarsal.

In particular, it is possible to «bring» the head of the metatarsal closer to the diaphyseal shaft of the metatarsal and thus compress them one on top of the other.

In one embodiment, the surgical instrumentation has at least one wire intended to be fixed to the diaphysis of the metatarsal, and the device for fastening the tool includes at least one hole formed passing through the proximal part of the frame in such a manner to allow the passage of said at least one wire.

It is thus possible to fix the tool on the diaphysis of the metatarsal by drilling a bore in the medial cortex of the diaphysis of the metatarsal according to a cross direction: by inserting the wire both in this bore and in the bore of the frame, the tool is immobilized along the translation axis.

According to one possibility, the frame of the tool includes, in its distal part, an actuator adapted to displace the movable body along the translation axis.

According to another possibility, the actuator of the tool includes a translation wheel making it possible to drive in rotation a threaded screw cooperating with a threaded hole formed in the movable body along the translation axis.

By actuating the translation wheel, the practitioner can therefore displace the movable body along the translation axis relative to the frame, and thus vary the intensity of the interfragmentary compression.

In one embodiment, the complementary device for securing the tool includes an indexing pin configured to cooperate with the indexing orifice of the plate of an implant as described above, so as to index the position of the implant relative to the tool with a view to secure the tool on the implant.

Alternatively, the pitch of the translation wheel is reversed, that is to say that a clockwise rotation of the wheel causes a proximal displacement of the movable body.

According to one possibility, the complementary device for securing the tool includes a securing rod, said securing rod having a threaded end and being configured to cooperate with the threaded hole of the securing device of an implant such as previously described, so as to removably attach the tool on said implant.

The indexing pin can thus be inserted into the indexing orifice of the implant to position the tool relative to the implant, and the threaded end of the securing rod can then be inserted into the threaded hole of the implant securing device, in order to attach the tool on the implant.

It should be noted that the securing rod also makes it possible to orientate the position of the tool in rotation with respect to the implant, once the indexing pin has been inserted into the indexing orifice.

According to another possibility, the securing rod of the tool is connected to a securing wheel making it possible to drive said securing rod in rotation, the securing wheel being arranged opposite the upper face of the movable body and the threaded end of the securing rod being disposed opposite the underside of the movable body.

Thanks to this securing wheel, it is thus possible for the practitioner to remotely manipulate the securing rod (and from the upper face of the tool): the practitioner can therefore fix the tool on the implant in a simple way and without requiring a large handling approach.

In one embodiment, the movable body of the tool includes at least one guide hole formed passing through it, the guide hole(s) being configured so that, when the tool is fixed on an implant as described above, these are located opposite the hole(s) of the implant keel and extend in a guiding direction collinear with that of said holes.

The very particular positioning of this or these guide holes makes it possible to guide the practitioner for the attachment of the implant on the diaphysis of the metatarsal using anchoring screws inserted into the hole(s) of the keel of said implant.

Indeed, once the tool is secured to the implant using the additional securing device, the hole(s) of the keel (invisible to the practitioner, the keel being inserted in the medullary canal of the diaphysis of the metatarsal) are located directly opposite the guide hole(s) of the guide: it is then sufficient to make bores in direction indicated by the guide hole(s) and then insert anchoring screws therein.

The practitioner can therefore easily identify the locations of the bores to be made without risk of error.

As a result, only very small incisions in the skin of the patient are necessary for fixing the implant according to the invention and the surgical technique is very minimally invasive.

According to one possibility, the surgical instrumentation includes at least one viewfinder configured to be inserted into at least one of the guide holes of the movable body of the tool and provided to guide a drilling or screwing instrument according to the guiding direction.

Such a viewfinder, once inserted in a guide hole, can make it possible to guide the positioning of the drills and screws used for fixing the implant to the diaphysis of the metatarsal.

The invention also concerns a surgical kit suitable for fixing a first bone fragment to a second bone fragment following a transverse osteotomy, including:

an implant as described above, and surgical instrumentation as described above.

It also concerns a surgical kit suitable for fixing a first bone fragment to a second bone fragment following a transverse osteotomy, including:

an implant as described above, at least two locked screws adapted to cooperate with the threaded holes of the plate, at least one locked screw adapted to cooperate with the hole in the intermediate portion, and at least one abutment screw adapted to cooperate with the hole(s) of the keel.

In one embodiment, the locked screws:

have a head of complementary shape respectively to the housing of the threaded holes of the plate and to the housing of the hole of the intermediate portion, and include self-tapping elements arranged at their end opposite to said head.

These locked screws can have a thread extending over almost their entire length and a threaded head also cooperating with the complementary housings of the threaded holes of the plate and of the intermediate portion of the implant, thus allowing a solid and reliable attachment with the implant.

The self-tapping elements make it easier to insert the locked screws into the bone of the head of the metatarsal and the diaphysis of the metatarsal.

According to one possibility, the abutment screws include a head having a collar adapted to abut against the medial cortex of the metatarsal when said abutment screws are inserted into the holes of the keel.

These abutment screws are intended to be screwed from the cortex of the metatarsal diaphysis and through the holes in the implant keel.

The presence of the collar allows the practitioner, during the insertion of an abutment screw, to identify the maximum insertion position of the latter because, when the collar is in contact with the medial cortex of the diaphysis of the metatarsal, the tightening torque increases sharply.

In this way, the practitioner can insert the abutment screws while having very poor visibility of their insertion site: this characteristic makes it possible to make the surgical technique of fixing the implant according to the minimally invasive invention.

According to one characteristic, the abutment screws have a thread whose width is comprised between 0.1 millimeter and 0.3 millimeter.

The presence of this particularly wide thread makes it possible to increase the size of the contact surface between the abutment screws and the cancellous bone of the metatarsal as well as the contact surface between the abutment screws and the hole(s) of the keel in which they are inserted.

In this way, this thread guarantees good grip of the abutment screws in the metatarsal and good coaxiality between them and the threaded holes of the implant.

According to one characteristic, the abutment screws are designed to be able to be inserted into the guide holes of the movable body of the tool.

Other characteristics and advantages of the present invention will become apparent on reading the detailed description below of a non-limiting example of implementation, made with reference to the appended figures in which:

FIG. 1 is a schematic dorsal view of the result of a transverse osteotomy,

FIG. 2 is a perspective view of an implant according to the invention,

FIG. 3 is a cross view of an implant according to the invention,

FIG. 4 is a sagittal section view of an implant according to the invention,

FIG. 5 is a top or cross view of an implant according to the invention fixed to a metatarsal, FIG. 6 is a detailed view of the keel of an implant according to the invention, FIG. 7 is a sagittal view (FIG. 7*a*) and a sectional view along the cross plane (FIG. 7*b*) of an implant according to a second embodiment of the invention, FIG. 8 is a detailed view of a locked screw, FIG. 9 is a detailed view of an abutment screw, FIG. 10 is a sagittal view of an implant according to the invention fixed to a metatarsal, FIG. 11 is a front view of an implant according to the invention fixed to a metatarsal, FIG. 12 is a view of a range including several implants according to the invention, FIG. 13 is a perspective view of a tool according to the invention, FIG. 14 is a lateral view of a tool according to the invention, FIG. 15 is a top view of a tool according to the invention, FIG. 16 is an illustration of the translation of the head of a metatarsal in the context of a transverse osteotomy, FIG. 17 is a view of a step of shaping the medullary canal of the diaphysis of a metatarsal, FIG. 18 is a view of a step of impacting an implant according to the invention in the medullary canal of the diaphysis of a metatarsal, FIG. 19 is a view of a step of piercing the head of a metatarsal, FIG. 20 is a view of a step of fixing an implant according to the invention on the head of a metatarsal, FIG. 21 is a view of a tool according to the invention fixed to an implant according to the invention, FIG. 22 is a view of a step of compressing the head of a metatarsal against the diaphyseal shaft of the same metatarsal, FIG. 23 is a view of a step of preparing the attachment of an implant according to the invention on the diaphysis of a metatarsal, FIG. 24 is a view of a step of fixing an implant according to the invention on the diaphysis of a metatarsal, FIG. 25 is a view of a step of preparing the attachment of an implant according to a second embodiment of the invention on the diaphysis of a metatarsal, FIG. 26 is a view of a step of preparing the attachment of two implants from a range of implants on the diaphysis of a metatarsal, FIG. 27 is a view of a step of drilling the diaphysis of a metatarsal, FIG. 28 is a view of a step of fixing an implant according to the invention on the head of a metatarsal.

FIG. 1 illustrates the result of a transverse osteotomy performed on a metatarsal in order to correct a hallux valgus.

FIG. 1*a* represents a metatarsal M and a first phalanx P of a foot affected by a hallux valgus, FIG. 1*b* representing the metatarsal M and the phalanx P at the end of the transverse osteotomy.

In FIG. 1*a*, the metatarsal M has a diaphysis 1, a head 2 and extends along a longitudinal axis M1.

The head 2 of the metatarsal M is strongly deflected «inward» of the foot, in a medial direction, and creates a bony protrusion which may be painful for the patient.

In order to treat this deformation, a rectilinear cut D was made in the diaphysis 1 of the metatarsal M, in a cross direction, orthogonal to the longitudinal axis M1.

The head 2 of the metatarsal M can then be displaced in translation with respect to the diaphysis 1 of the metatarsal M in this same cross direction, so as to attenuate the bony protrusion and reposition the first phalanx P in a configuration substantially collinear with the longitudinal axis M1, as can be seen in FIG. 1*b*.

Once this displacement has been made, the head 2 of the metatarsal M is temporarily held in its new position by a Kirschner wire B, inserted into the intramedullary part of the diaphysis 1 of the metatarsal M.

In order to permanently fix the head 1 of the metatarsal M in this new position and allow osteosynthesis, it is possible to use an implant 3 according to the invention, visible in FIG. 2 in perspective, and in FIG. 3 in a cross view.

This implant 3 includes a keel 4, intended to be inserted into the medullary canal of the diaphysis 1 of the metatarsal M, a plate 5, intended to be fixed on the head 2 of the metatarsal M, and an intermediate portion 6 connecting the keel 4 to plate 5.

The keel 4 extends along a longitudinal axis 41 and has a generally cylindrical shape, centered on the longitudinal axis 41.

It should be noted that the keel 4 has a proximal end 42 of a section lower than the cylindrical portion of said keel 4.

The plate 5 has a flat lateral face 51, adapted to be brought into contact with the medial face of the head 2 of the metatarsal M, is configured so that the longitudinal axis 41 is orthogonal to a direction N normal to this lateral face 51 of the plate 5.

The advantages of this configuration will appear later.

The intermediate portion extends in the continuity of the keel 4 along the longitudinal axis 41 and makes the junction between this keel 4 and the plate 5.

This intermediate portion thus has a conical (or frusto-conical) shape centered on the longitudinal axis 41: this conical shape gives the implant 3 good flexural strength when the latter is in position, fixed on the metatarsal M.

It also participates in maintaining the implant 3 in the medullary canal of the diaphysis 2 of the metatarsal M, by a «press-fit» effect on the walls of this medullary canal.

The implant 3 further includes an inner conduit 7, visible in FIG. 4, of circular section and centered on the longitudinal axis 41.

This inner conduit 7 opens out at the proximal end 42 of the keel 4 and at a distal end 61 of the intermediate portion 6.

The function and utility of this inner conduit 7 will be further detailed below.

The implant 3 can be fixed to the metatarsal M, as represented in FIG. 5, by means of anchoring screws inserted into the bone of the metatarsal M and cooperating with holes formed in the implant 3.

In particular, once the implant 3 has been inserted into the medullary canal 11 of the diaphysis 1 of the metatarsal M and the lateral face 51 of the plate 5 brought into contact with the head 2 of the metatarsal M, the position of the implant 3 is fixed by:

two abutment screws 8 inserted in the diaphysis 1 of the metatarsal M and cooperating with holes 43 which are formed passing through the keel 4, at least two locking screws 9 inserted in the head 2 of the metatarsal M and cooperating with threaded holes 52 which are formed passing through the plate 5, and a locking screw 9 inserted in the diaphysis 1 of the metatarsal M and cooperating with a threaded hole 62 which is formed passing through the intermediate portion 6.

The holes 43 and the threaded holes 52 are formed passing through the keel 4 and the plate 5 respectively in the direction N, orthogonal to the longitudinal axis 41: this orthogonality makes it possible in particular to effectively block any rotational movement of the implant 3 about the longitudinal axis 41.

The threaded hole 62, as visible in FIG. 3, extends in a direction 63 oblique with respect to the direction N, this direction 63 forming with the lateral face 51 of the plate 5, in cross view, an angle α whose measurement is strictly less than 90°.

It will be noted that the direction 63 forms an angle α identical with the longitudinal axis 41.

For example, the measurement of the angle α is, in this embodiment, equal to 70°.

Due to the obliquity of this threaded hole 62, the screwing of the locked screw 9 therein has the effect of compressing the head 2 of the metatarsal M against the diaphyseal shaft 12 of the metatarsal M, and thus increase the interfragmentary pressure.

As can be seen in FIG. 4, the threaded holes 52 have a housing 521 opening onto the medial face 53, opposite to the lateral face 51, of the plate 5.

This housing 521 is adapted to receive the head 91 of a locked screw 9, so that, when this locked screw 9 is fully screwed into the threaded hole 521, the head 91 thereof is received in the housing 521 and does not protrude from the medial face 53 of the plate 5, as visible in FIG. 3: in this way, the implant 3 is the least invasive possible.

Likewise, the threaded hole 62 includes an identical housing 521, so that the locked screw 9 does not protrude from the intermediate portion 6.

The holes 43 have a medial mouth 431 provided with a peripheral chamfer 432 visible in FIGS. 6a and 6b.

This peripheral chamfer 432 makes it possible to facilitate the insertion into the holes 43 through the medial mouth 431 of drills making the holes in the diaphysis of the metatarsal M in which the abutment screws 8 are then introduced, as well as the introduction of the abutment screws 8 themselves.

FIGS. 7a and 7b show a second embodiment of the implant 3 according to the invention, in which the intermediate portion 6 does not have a threaded hole.

On the other hand, the keel 4 has two through holes 43 each extending in a different direction:

a first hole 433, extending in a direction 4331 parallel to the direction normal (N) to the lateral face 53 of the plate (5), and a second hole 434, extending in a direction 4341 not parallel to the direction normal (N) to the lateral face 53 of the plate (5), forming an angle β with the longitudinal axis 41.

This second hole fulfills the same functions as the threaded hole 62 of the first embodiment described by the preceding FIGS. 1 to 7, namely to fix the implant 3 on the diaphysis 1 of the metatarsal M by screwing an anchoring screw and compressing the head 2 of the metatarsal M against the diaphyseal shaft 12 of the metatarsal M (and thus increasing the interfragmentary pressure), due to the obliquity of the direction 4341.

The replacement of the threaded hole 62 of the intermediate portion 6 by the second hole 434 of the keel 4 makes it possible to make the surgical technique less invasive, access to the threaded hole 62 (to perform a drilling step, then a step of screwing an anchoring screw) requiring a larger approach than access to the second hole 434.

It will be noted that, as visible in FIG. 7b, the first hole 433 and the second hole 434 have, in the same way as the previous holes 43, a medial peripheral chamfer 432 fulfilling the same function.

Furthermore, an alternative embodiment can obviously be envisaged, in which the positions on the keel 4 of the first hole 433 and of the second hole 434 are reversed with respect to the embodiment represented by the preceding FIGS. 7a and 7b, the second hole 434 then being closer to the intermediate portion 6 and to the plate 5 than the first hole 433.

FIG. 8 details the particular characteristics of the locked screws 9.

Each locked screw 9 has a head 91 and a threaded rod 92, the threaded rod having a thread over almost its entire length up to one end 921.

The head 91 also has a thread and is of complementary shape to the housings 521: in this way, the locked screws 9 are firmly fixed to the implant 3, and the movements of the latter once in position are extremely limited.

The threaded rod 92 also includes, near its end 921, self-tapping elements 922, making it possible to facilitate the insertion of the locked screws 9 into the bone of the diaphysis 1 of the metatarsal M or of the head 1 of the metatarsal M.

FIG. 9 represents an abutment screw 8, whose shape is specially adapted to the attachment of the implant 3 in the diaphysis 1 of the metatarsal M.

This abutment screw 8 has a head 81 and a threaded rod 82.

The threaded rod 82 has a wide thread, for example having a thickness E of about 0.2 millimeters, making it possible to provide a large contact surface between the abutment screw 8 and the bone of the diaphysis 1 of the metatarsal M on the one hand, and between the abutment screw 8 and the keel 4, in which the holes 43 are formed, on the other hand.

This large contact surface thus makes it possible to ensure the good coaxiality of the abutment screws and the holes 43, as well as a strong anchoring in the bone of the diaphysis 1 of the metatarsal M.

On the other hand, the head 81 of the abutment screw 8 is also threaded and has a collar 811, whose diameter is greater than that of the external thread 812 of the head 81.

In this embodiment, the difference between the diameter of the collar 811 and that of the external thread 812 is comprised between 1 millimeter and 3 millimeters, for example 1.2 millimeters.

This collar 811 is intended to rest on the outer cortex of the diaphysis 1 of the metatarsal M when screwing the abutment screw 8 into the holes 43 of the keel, and its usefulness will be explained below.

The particular structure of the implant 3 has the advantage of allowing the practitioner to easily position the head 2 of the metatarsal M with respect to the diaphysis 1 of the metatarsal M with precision, by offering the possibility of displacing (before the insertion of the locked screws 9 and abutment screws 8) this head 2 of the metatarsal M according to three degrees of freedom.

First, as can be seen in FIG. 10, it is possible to vary the height of the head 2 of the metatarsal M in the dorsoplantar plane: once the keel 4 is inserted into the medullary canal 11 of the diaphysis 1 of the metatarsal M, it suffices to vary the insertion location of the screws 9 on the head 2 of the metatarsal M to raise or lower this head 2 of the metatarsal M relative to the diaphysis 1 of the metatarsal M.

For example, in FIG. 10a, the identified locked screws 9' are placed on the head 2 of the metatarsal M at a distance $D_1$ from a dorsal end 21 of the head 2 of the metatarsal M greater than the distance $D_2$ measured in FIG. 10b: the locked screws 9' being further in this FIG. 10a from the dorsal end 21, the head 2 of the metatarsal M is thus positioned higher in the dorsoplantar plane in the configuration of FIG. 10a than in that of FIG. 10b.

Second, the fact that the keel 4 has the shape of a solid of revolution (in particular, cylindrical shape) allows the practitioner to make the implant 3 perform a rotational movement about the longitudinal axis 41, without deforming the medullary canal 11 of the diaphysis 1 of the metatarsal M in which the keel 4 is inserted.

As a result, it is possible to vary the position of the head 2 of the metatarsal M in axial rotation about the longitudinal axis 41, even after inserting the keel 4 into the medullary canal 11 of the diaphysis 1 of the metatarsal M.

It is important to note that this movement, authorized by the particular shape of the keel 4, is impossible to achieve with the various implants known from the state of the art.

For example, in FIG. 11, the head 2 of the metatarsal M has undergone between the configuration of FIG. 11a and that of FIG. 11b a rotational movement about the longitudinal axis 41 in the clockwise direction.

Finally, FIG. 12 represents a range G of implants including several implants 3 according to the invention, each of these implants 3 having a different lateral offset distance DL, this lateral offset distance DL (also called «step») being measured between the longitudinal axis 41 and the lateral face 51 of the plate 5.

For example, the range G includes in this embodiment four implants 3 whose lateral offset distance varies between 0 millimeters (so-called «neutral» implant, on the left in FIG. 12) and 6 millimeters (implant 3 on the right in FIG. 12).

By selecting an implant from the range G rather than another, it is thus possible to vary the position of the head 2 of the metatarsal M in the medial/lateral plane.

In conclusion, the particular structure of the implant 3 according to the invention allows the practitioner to select and vary the position of the head 2 of the metatarsal M:

in the medial/lateral plane, by selecting a particular implant from the range G during the surgical operation, in the dorsoplantar plane, by selecting the position of the insertion site of the locked screws 9 on the head 2 of the metatarsal M, once the keel 4 has been inserted into the medullary canal 11 of the diaphysis 1 of the metatarsal M, and in axial rotation about the longitudinal axis 41, by causing the implant 3 to perform a rotational movement about this same longitudinal axis 41.

This freedom of positioning the head 2 of the metatarsal M relative to the diaphysis 1 of the metatarsal M according to 3 degrees of freedom thus allows the practitioner to provide a «customized» correction for each patient, adapted to the particular characteristics of their hallux-valgus.

The following FIGS. 13 to 15 represent a tool 10 suitable for preparing the attachment, on the metatarsal M, of an implant 3 according to the invention as described above.

This tool 10, specially adapted to the manipulation of the implant 3, makes it possible to guide the practitioner during the attachment of the implant 3 on the metatarsal M and to make the used surgical technique less invasive.

In particular, the tool 10 aims at facilitating the following operations:

manipulation of the implant to position the head 2 of the metatarsal M relative to the diaphysis 1 of the metatarsal M, application of interfragmentary compression, and insertion of the abutment screws 8 in the holes 43 of the keel 4.

This tool 10 includes a frame 101, in particular having two parallel slides 1011.

The tool also includes a movable body 102 displaceable, as can be seen in the figure, in translation along the slides 1011 along a translation axis 1020.

The frame 101 includes a translation wheel 1012 making it possible to rotatably drive a threaded rod 1013 cooperating with a threaded hole made in the movable body 102: by actuating this translation wheel 1012, it is thus possible to drive the movable body 102 in translation along the translation axis 1020.

For example, between the configurations of FIGS. 15a and 15b, the movable body has been displaced by a translation distance T.

Moreover, the frame 101 also includes two holes 1014 which are formed passing through a distal end 1015.

These holes 1014 are adapted to receive a Kirschner wire also inserted into the bone of the diaphysis 1 of the metatarsal M, thus hooking the tool 10 to this same diaphysis 1 of the metatarsal M.

This hooking of the tool 10 on the diaphysis 1 of the metatarsal M will allow the practitioner to exert an inter-fragmentary compression thanks to the translation wheel, as this will be further detailed below.

The movable body 102 includes an indexing pin 1021 and a securing rod 1022 making it possible to secure the tool 10 to the implant 3.

Indeed, as can be seen in FIG. 4, the plate 5 of the implant 3 has in a complementary manner an indexing orifice 54 and a threaded hole 55, which are both formed passing between the lateral face 51 and the medial face 53.

The indexing pin 1021 is adapted to be inserted into the indexing hole 54 and makes it possible to position the tool 10 relative to the implant 3.

The securing rod 1022 includes a threaded end 1023 adapted to cooperate with the threaded hole 55 and makes it possible to fix, in a removable manner, the tool 10 on the implant 3.

A detailed view of this attachment of the tool 10 on the implant 3 will be given below.

The securing rod 1022 also cooperates with a securing wheel 1024 making it possible to manipulate this securing rod 1022 from an upper face 103 of the tool 10, the threaded end 1023 of the securing rod 1022 being located opposite a lower face 1024 of the tool 10.

Thus, the practitioner can fix the tool 10 on the implant 3 in a minimally invasive approach, without having physical access to the indexing hole 54 or to the threaded hole 55.

It should be noted that, in the represented embodiment, the threaded hole 55 is identical to the threaded holes 52: this threaded hole 55 can thus be used, once the tool 10 has been disconnected from the implant 3, to insert a locked screw 9 in order to strengthen the attachment of the plate 5 on the head 2 of the metatarsal M.

Finally, the movable body 102 has two guide holes 1025, positioned so that, when the tool 10 is fixed on the implant 3, these two guide holes are located opposite the holes 43 of the keel 4.

These guide holes will thus serve, as will be detailed later, to guide the practitioner during the insertion of the abutment screws 8 into the holes 43.

The following FIGS. 16 to 28 make it possible to detail the surgical method used to fix the implant 3 according to the invention on the metatarsal M, using the tool 10.

FIG. 16 represents the result of a transverse osteotomy identical to that detailed in FIG. 1 above, at the end of which the head 2 of the metatarsal M has undergone a cross translation (in the medial/lateral plane) with respect to the diaphysis 1 of the metatarsal M following the rectilinear cut D, for example carried out using a bone saw.

The head 2 of the metatarsal M is thus in a position away from the longitudinal axis M1 of the diaphysis 1 of the metatarsal M.

This head 2 of the metatarsal M is maintained in its new position by a Kirschner wire B, inserted into the medullary canal 11 of the diaphysis 1 of the metatarsal M and extending along the longitudinal axis M1.

Once the wire B has been put in place, the practitioner makes, by drilling, a tunnel T about the wire B, then prepares this tunnel T with a shaper 100 to receive the implant 3 according to the invention, as visible in FIG. 17.

This shaper 100 makes it possible, by being inserted into the tunnel T, to push back the cancellous bone forming the walls of this tunnel T, in order to adapt the shape of the latter to that of the implant 3.

The implant 3 according to the invention is then «threaded» onto the wire B and introduced into the tunnel T: the wire B is in fact introduced into the inner conduit 7 of the implant 3 through the proximal end 42 of the keel 4, and opens at the level of the distal end 61 of the intermediate portion 6: thanks to the presence of the inner conduit 7, the insertion of the implant 3 in the medullary canal 11 of the diaphysis 1 of the metatarsal M is perfectly guided and very precise.

It will also be noted that, in this configuration, the longitudinal axis 41 of the implant 3 and the longitudinal axis M1 of the metatarsal M are confounded.

Once the implant has been inserted into the tunnel T, the practitioner can use a surgical impactor 200, as represented in FIG. 18, in order to drive the keel 4 of the implant 3 more deeply into the diaphysis 1 of the metatarsal M.

This surgical impactor 200 has a structure specially adapted to the implant 3 according to the invention.

It indeed includes a securing rod adapted to cooperate with the threaded hole 52 of the plate 5 furthest from the intermediate portion 6, which can be manipulated by means of a wheel 201, and has a casing 202 matching the shape of the plate 5: it is thus possible to index the surgical impactor to the implant 3 by making the respective complementary shapes of the plate 5 and the casing 202 coincide, then to secure this surgical impactor 200 to the implant 3 by screwing the securing rod into one of the holes 52.

Once the surgical impactor 200 thus positioned and fixed to the implant 3, the practitioner can perform the actual impaction step of the implant 3 in the medullary canal 11 of the diaphysis 1 of the metatarsal M.

It should be noted that it is during these steps of inserting and impacting the implant 3 in the diaphysis 1 of the metatarsal M that the practitioner fixes, by the choice of the value of the offset distance DL of the implant 3, the position of the head 2 of the metatarsal M in the medial/lateral plane, as previously described.

Once the implant 3 has been impacted, the practitioner makes two holes through the threaded holes 52 of the plate 5 using a drill 300 and a viewfinder 301, as represented in FIG. 19.

The locking screws 9 are then screwed (see FIG. 20) in these made bores, cooperating with the threaded holes 52, so as to fix the plate 5 on the cortex of the head 2 of the metatarsal M.

It is at this stage that, as previously described, the practitioner selects the position of the head 2 of the metatarsal M in the dorsoplantar plane as a function of the location on this head 2 of the metatarsal M of the bores intended to receive the locked screws 9.

The wire B is then removed from the diaphysis 1 of the metatarsal M.

In order to complete the attachment of the implant on the metatarsal M, the practitioner can then use the tool 10 as illustrated in FIG. 21.

In this FIG. 21, the tool 10 is secured to the implant 3 via the indexing pin 1021 and the securing rod 1022 (not visible in this FIG. 21) of the movable body 102: the indexing pin 1021 is introduced into the indexing orifice 54 located on the plate 5 of the implant 3 and the threaded end 1023 of the securing rod 1022 cooperates with the threaded hole 55 also located on the plate 5 of the implant 3.

In order to achieve this attachment of the tool 10 on the plate 5 of the implant 3, the practitioner can in particular use the securing wheel 1024, making it possible to screw the threaded end 1023 into the threaded hole 55.

The tool 10 is then fixed on the head 2 of the metatarsal M via the plate 5.

The practitioner can then displace the tool 10 in rotation about the longitudinal axis 41: this rotational movement consequently drives the implant 3 and the head 2 of the metatarsal M in rotation about the same longitudinal axis 41.

By means of the tool 10, the practitioner can therefore select (as illustrated by FIG. 11) the position of the head 2 of the metatarsal M in axial rotation about the longitudinal axis 41.

The tool 10 is further fixed on the diaphysis 1 of the metatarsal M by a Kirschner wire B inserted into one of the orifices 1014 formed at the proximal end 1015 of the frame 101, this wire B' also being inserted through the cortex of the diaphysis 1 of the metatarsal M.

Thus, the movable body 102 is fixed to the head 2 of the metatarsal M via the securing rod 1022, the plate 5 and the locking screws 9, while the frame is fixed to the diaphysis 1 of the metatarsal M via the wire B'.

In addition, the tool 10 is shaped so that, when the latter is fixed to the implant 3, the translation axis 1020 of the tool is parallel to the longitudinal axis 41 of the implant.

Therefore, any translational movement of the movable body 102 relative to the frame 101 along the translation axis 1020 results in a translation of the head 2 of the metatarsal M relative to the diaphysis 1 of the metatarsal M along the longitudinal axis 41.

Thus, by actuating the translation wheel 1012, the practitioner can vary the intensity of the interfragmentary compression between the head 2 of the metatarsal M and the diaphyseal shaft of the metatarsal M.

This manipulation of the translation wheel 1012 is illustrated in FIG. 22.

Once the desired interfragmentary compression has been reached, the practitioner can use the guide holes 1025 of the movable body 2 to introduce the abutment screws 8 into the holes 43 of the keel, in order to block the implant 3 in rotation about the longitudinal axis 41.

Indeed, the tool 10 is shaped so that, when the latter is fixed on the implant 3, the guide holes 1025 are located opposite the holes 43 of the keel 4: by drilling according to the guide directions 1026 indicated by guide holes 1025, the practitioner is then certain to reach holes 43.

As illustrated by FIG. 23, the practitioner can insert viewfinders 400 into the guide holes 1025 making it possible to materialize the guide directions 1026.

After making two small cutaneous cuts E at the intersection of the guiding directions and the outer surface of the patient foot, the practitioner can insert drills in the viewfinders 400 to make holes in the diaphysis 1 of the metatarsal M according to the guide directions 1026, then tighten the abutment screws 8 using a bit 401 in these same holes, as illustrated in FIG. 24.

It is important to note that the insertion locations of the abutment screws 8 in the diaphysis 1 of the metatarsal M are invisible to the practitioner: the practitioner therefore «blindly» screws the abutment screws 8 in the holes made in the guiding directions 1026 until the collar 811 of the abutment screws come into contact with the cortex of the diaphysis 1 of the metatarsal M.

At this moment, the tightening torque of the abutment screws 8 increases sharply, indicating to the practitioner that the latter are sufficiently introduced into the diaphysis 1 of the metatarsal M.

Thus, thanks to the guide holes 1025 and the particular shape of the abutment screws 8, it is easy for the practitioner to make, in a minimally invasive manner, the bores necessary for the insertion of the abutment screws 8 making it possible to fix the implant 3 at the diaphysis 1 of the metatarsal M and to block its rotation about the longitudinal axis 41.

FIG. 25 represents the same step of making holes in the diaphysis 1 of the metatarsal M, using a drill 402, in a second embodiment of the invention, when the implant 3 does not have a threaded hole 62 formed in the intermediate portion 6, but a second hole 434 formed of the keel 4 instead.

As described by the preceding FIG. 7*b*, this second hole 434 extends in a direction 4341 which is not orthogonal to the longitudinal axis 41 (inclined by a measurement angle β relative to the latter).

In order to be able to guide the practitioner during the drilling operation through this second hole 434, the shape of the tool 10 is adapted accordingly: this tool 10 has a guide hole 1027 positioned opposite the second hole 434 and extending in the direction 4341 when the tool 10 is fixed on the implant 3.

Thus, the guide hole 1027 indicates a guide direction 1028 collinear with the direction 4341 and not parallel to the guide direction 1026 indicated by the other guide hole 1025: this modification of the shape of the tool 10, in order to make the guide direction 1028 of the guide hole 1027 coincide with the oblique direction 4341, therefore allows the practitioner to be guided, in a manner identical to the embodiment described by the preceding FIGS. 21 to 24, when the intermediate portion 6 does not have an oblique threaded hole 62.

It will be noted that it is also particularly advantageous to be able to fix the same tool 10 on several implants of a range of implants in which each implant has (as previously described) a different lateral offset distance DL.

Yet, the variation of this lateral offset distance DL within such a range of implants can have an influence on the positioning of the threaded hole(s) of the keel 4 if at least one of them extends in a direction not orthogonal to the longitudinal axis 41.

For example, FIG. 26 illustrates the attachment of the same tool 10 on the implant 3 and on a second implant 3', this implant 3' having a lateral offset distance DL' (measured between a lateral face 51' of a plate 5' and a longitudinal axis 41' of the implant 3') greater than the lateral offset distance DL of the implant 3 (measured between the lateral face 51 of the plate 5 and the longitudinal axis 41 of the implant 3).

The implant 3 has, as described by the preceding FIG. 25, a second hole 434 formed of the keel 4 and extending in the guiding direction 1028 of the guide hole 1027 of the tool 10 when this tool 10 is fixed on the implant 3.

Similarly, the implant 3' has a second hole 434' formed in a keel 4' and extending in the same guiding direction 1028 of the tool 10 when this tool 10 is fixed on the implant 3': so that the collinearity of this second hole 434' with the guide hole 1027 is ensured while the lateral offset distance DL' is greater than the lateral offset distance DL, it is necessary to modify the position of this second hole 434' on the keel 4' relative to that of the second hole 434 on the keel 4 of the implant 3.

Indeed, the keel 4' being closer to the frame 101 of the tool 10 than the keel 4, the second hole 434' must be positioned closer to the plate 5' than the second hole 434 of the plate 5.

Consequently, the implant 3' has a spacing distance DE' (measured between a proximal end 56' of the plate 5' and the second hole 434') less than one spacing distance DE of the implant 3 (measured between a proximal end 56 of the plate 5 and the second hole 434').

Thus, within a range of implants each having a different lateral offset distance, it is necessary to adapt as a function of the latter, the position of the hole(s) made of the keel of each implant when they extend in a direction not orthogonal to the longitudinal axis of each implant, so that this or these holes are arranged vis-à-vis the guide hole(s) of the tool 10 when each of the implants is fixed to this same tool 10, in order to guide the practitioner in its drilling and screwing operations.

The tool 10 can then be detached from the implant 3, by manipulating the securing wheel 1024.

As represented in FIG. 27, the practitioner can then insert an viewfinder 500 into the orifice 62 of the intermediate portion of the implant 3, and introduce therein a drill 501 so as to make a bore through the lateral cortex of the diaphysis 1 of the metatarsal M.

A locking screw 9', cooperating with the threaded hole 62 can then be screwed into this same bore.

As previously described, this locked screw 9' inserted in the threaded hole has a direction 63 oblique with respect to those of the abutment screws 8 and of the locking screws 9 (orthogonal to the longitudinal axis 41) and makes it possible to further strengthen the interfragmentary compression between the head 2 of the metatarsal M and the diaphysis 1 of the metatarsal M.

The locked screw 9' also has the function of stabilizing the keel 4 in translation in the medio-lateral direction.

Finally, in this particular embodiment of the invention, the threaded hole 55 having served to fix the tool 10 on the implant 3 being identical to the threaded holes 52 in which the locked screws 9 are inserted: it is then possible for the practitioner to drill through this threaded hole 55, then introduce a new locked screw 9 using a tip 600 (visible in FIG. 28) in order to strengthen the fixing of the plate 5 on the head 2 of the metatarsal M.

The invention claimed is:

1. An implant, of the intramedullary implant type, suitable for fixing a first bone fragment on a second bone fragment, said implant including:
   a plate having a flat side face shaped to be fixed on the second bone fragment,
   a keel shaped to be inserted into a medullary canal of the first bone fragment, the keel being a solid of revolution centered on a longitudinal axis, and said longitudinal axis being parallel to a lateral face of the plate, and
   an intermediate portion, connecting said plate to said keel, wherein the plate includes:
      at least two threaded holes passing through the plate between the lateral face and an opposite medial face, wherein one or more of the at least two threaded holes is configured as a securing device making it possible to releasably secure said implant to a tool adapted to prepare the attachment of said implant on the metatarsal; and
      an indexing orifice formed in the plate and opening onto the medial face, the indexing orifice configured to receive an indexing pin in the tool allowing to index a position of the implant relative to the tool for securing the tool on the implant.

2. The implant according to claim 1, wherein the keel has a cylindrical shape.

3. The implant according to claim 1, wherein each of said at least two threaded holes have a housing opening onto the medial face and adapted to receive the head of an anchoring screw.

4. The implant according to claim 3, wherein the at least two threaded holes extend in a direction normal to the lateral face.

5. The implant according to claim 1, wherein the threaded hole of the securing device:
   crosses the plate between the medial face and the lateral face, has a housing opening onto the medial face adapted to receive the head of an anchoring screw.

6. The implant according to claim 1, wherein the keel has at least one hole passing through said keel in a cross direction to the longitudinal axis and adapted to receive an anchoring screw.

7. The implant according to the claim 6, wherein the at least one hole of the keel extend in a direction normal to the lateral face of the plate.

8. The implant according to claim 7, wherein the at least one hole of the keel have a medial mouth provided with a peripheral chamfer.

9. The implant according to claim 6, wherein the keel has at least two holes passing through said keel and adapted to receive an anchoring screw, the first one of the at least two holes extending in a direction parallel to the direction normal to the lateral face of the plate, and a second one of the at least two holes extending in a direction not parallel to said direction normal to the lateral face of the plate.

10. The implant according to claim 1, wherein the keel includes an inner conduit centered on the longitudinal axis, said internal conduit opening at a proximal end of the keel, passes through the intermediate portion and opens at a distal end of said intermediate portion.

11. The implant according to claim 1, wherein the intermediate portion has a conical shape centered on the longitudinal axis.

12. The implant according to claim 1, wherein the intermediate portion includes a hole which is formed passing through said intermediate portion, said hole extending in a direction not parallel to the direction normal to the lateral face of the plate.

13. The implant according to claim 12, wherein the hole of the intermediate portion is a threaded hole which has a housing opening onto a medial face of the intermediate portion, said housing being adapted to receive the head of an anchoring screw.

14. The implant according to claim 13, wherein the threaded hole of the intermediate portion extends in a direction forming an angle with the lateral face of the plate whose measurement is comprised between 60° and 80°.

15. A range of implants comprising several implants according to claim 1, said implants each having a lateral offset distance, separating the lateral face of the plate from the longitudinal axis, of distinct measurement.

16. The range of implants according to claim 15, wherein the implants have a lateral offset distance whose measurement is comprised between 0 millimeters and 10 millimeters.

17. The range of implants according to claim 15, wherein the keel of each implant in the range implants includes an inner conduit centered on the longitudinal axis, said internal conduit opening at a proximal end of the keel and passes through the intermediate portion and opens at a distal end of said intermediate portion, and wherein each of the conduits have a spacing distance, separating a proximal end of the plate from the inner conduit of distinct measurement.

18. A surgical instrumentation including a tool suitable for preparing the attachment, on a bone, of an implant according to claim 1, said tool including:

a frame, having a distal part and a proximal part, a movable body, having a lower face and an upper opposite face, including an indexing pin adapted to cooperate with the indexing orifice of the plate so as to index the position of the implant relative to the tool, and a complementary securing device adapted to cooperate with the securing device of the plate so as to fix the tool on the implant, said movable body being displaceable in translation relative to the frame along a translation axis parallel to the longitudinal axis of the implant when the tool is fixed on the implant, and a hooking device making it possible to fix said frame on the first bone fragment to which the implant is also fixed.

19. The surgical instrumentation according to claim 18, including at least one wire intended to be fixed on the first bone fragment, and in which the hooking device of the tool includes at least one bore which is formed passing through the proximal part of the frame so as to allow the passage of said at least one wire.

20. The surgical instrumentation according to claim 18, wherein the frame of the tool includes, in its distal part, an actuator adapted to displace the movable body according to the translation axis.

21. The surgical instrumentation according to claim 20, wherein the actuator of the tool includes a translation wheel making it possible to drive in rotation a threaded screw cooperating with a threaded hole formed in the movable body along the translation axis.

22. The surgical instrumentation according to claim 18, wherein each of said at least two threaded holes have a housing opening onto the medial face and adapted to receive the head of an anchoring screw, wherein the at least two threaded holes extend in a direction normal to the lateral face, and wherein the securing device indexes the position of the implant relative to the tool with a view to secure the tool on the implant.

23. The instrumentation according to claim 18, wherein the complementary securing device for securing the tool includes a securing rod, said securing rod having a threaded end and being configured to cooperate with the securing device of the plate, wherein the one or more threaded holes of the securing device:

crosses the plate between the medial face and the lateral face, has a housing opening onto the medial face adapted to receive the head of an anchoring screw, so as to removably fix the tool on said implant.

24. The surgical instrumentation according to claim 23 wherein the securing rod of the tool is connected to a securing wheel making it possible to drive said securing rod in rotation, the securing wheel being disposed opposite the upper face of the movable body and the threaded end of the securing rod being disposed opposite the lower face of the movable body.

25. The surgical instrumentation according to claim 18, wherein the movable body of the tool includes at least one guide hole formed passing through, the at least one guide hole being configured so that, when the tool is fixed on the implant, wherein the at least one hole of the keel extend in a direction normal to the lateral face of the plate, the at least one guide hole is located opposite the at least one hole of the keel of the implant and extend in a guiding direction collinear with that of said at least one hole.

26. The surgical instrumentation according to claim 25, including at least one viewfinder configured to be inserted into at least one of the at least one guide hole of the movable body of the tool and provided for guiding a drilling or screwing instrument along the guiding direction.

27. A surgical kit suitable for fixing a first bone fragment on a second bone fragment following a transverse osteotomy, including:

an implant in accordance with claim 1, and surgical instrumentation according including a tool suitable for preparing the attachment, on a bone of the implant, said tool including:

a frame, having a distal part and a proximal part, a movable body, having a lower face and an upper opposite face, including an indexing pin adapted to cooperate with the indexing orifice of the plate so as to index the position of the implant relative to the tool, and a complementary securing device adapted to cooperate with the securing device of the plate so as to fix the tool on the implant, said movable body being displaceable in translation relative to the frame along a translation axis parallel to the longitudinal axis of the implant when the tool is fixed on the implant, and a hooking device making it possible to fix said frame on the first bone fragment to which the implant is also fixed, including at least one wire intended to be fixed on the first bone fragment, and in which the hooking device of the tool includes at least one bore which is formed passing through the proximal part of the frame so as to allow the passage of said at least one wire.

28. The surgical kit suitable for fixing a first bone fragment on a second bone fragment following a transverse osteotomy, including:

an implant according to claim 3, wherein the keel has at least one hole passing through said keel in a cross direction, to the longitudinal axis and adapted to receive an anchoring screw, and wherein the intermediate portion includes a hole which is formed passing through said intermediate portion, said hole extending in a direction not parallel to the direction normal to the lateral face of the plate, at least two locked screws adapted to cooperate with the at least two threaded holes of the plate, at least one locked screw adapted to cooperate with the hole of the intermediate portion, and at least one abutment screw adapted to cooperate with the at least one hole of the keel.

29. The surgical kit according to claim 28, having the implant, wherein the threaded hole of the securing device:

crosses the plate between the medial face and the lateral face, has a housing opening onto the medial face adapted to receive the head of an anchoring screw, and wherein the hole of the intermediate portion is a threaded hole which has a housing opening onto a medial face of the intermediate portion, said housing being adapted to receive the head of an anchoring screw, and the locked screws:

have a head of complementary shape respectively to the housing of the at least two threaded holes of the plate and to the housing of the hole of the intermediate portion, and include self-tapping elements arranged at their end opposite to said head.

30. The surgical kit according to claim 28, wherein the at least one abutment screw includes a head having a collar adapted to abut against the medial cortex of the first bone fragment when said at least one abutment is inserted into the at least one hole of the keel.

31. A surgical instrumentation including a tool suitable for preparing the attachment of an implant on a bone, said implant including:

a plate having a flat side face shaped to be fixed on the second bone fragment and including at least two threaded holes passing through the plate between a lateral face and an opposite medial face, each of said at least two threaded holes having a housing opening onto the medial face and adapted to receive the head of an anchoring screw, wherein the at least two threaded holes extend in a direction normal to the lateral face, a keel shaped to be inserted into a medullary canal of the first bone fragment, the keel being a solid of revolution centered on a longitudinal axis, and said longitudinal axis being parallel to the lateral face of the plate, and an intermediate portion, connecting said plate to said keel, wherein the plate includes a securing device making it possible to releasably secure said implant to a tool adapted to prepare the attachment of said implant on the metatarsal, the securing device comprising an indexing hole and a threaded hole formed in the plate and opening onto the medial face so as to index the position of the implant relative to the tool; and said tool including:

a frame, having a distal part and a proximal part, a movable body, having a lower face and an upper opposite face, including a complementary securing device comprising an indexing pin adapted to cooperate with the securing device of the plate so as to fix the tool on the implant, said movable body being displaceable in translation relative to the frame along a translation axis parallel to the longitudinal axis of the implant when the tool is fixed on the implant, and a hooking device making it possible to fix said frame on the first bone fragment to which the implant is also fixed.

\* \* \* \* \*